(12) United States Patent
Schraut et al.

(10) Patent No.: US 11,166,816 B2
(45) Date of Patent: Nov. 9, 2021

(54) CUFF CONFIGURATIONS FOR PROSTHETIC HEART VALVE

(71) Applicant: St. Jude Medical, Cardiology Division, Inc., St. Paul, MN (US)

(72) Inventors: Julia A. Schraut, Shoreview, MN (US); Peter N. Braido, Wyoming, MN (US); Ramji T. Venkatasubramanian, Maple Grove, MN (US); Aditee Kurane, Oakdale, MN (US); Mina S. Fahim, Shoreview, MN (US); Jaishankar Kutty, Oakdale, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 345 days.

(21) Appl. No.: 16/156,492

(22) Filed: Oct. 10, 2018

(65) Prior Publication Data

US 2019/0038409 A1 Feb. 7, 2019

Related U.S. Application Data

(63) Continuation of application No. 14/745,840, filed on Jun. 22, 2015, now Pat. No. 10,136,992, which is a
(Continued)

(51) Int. Cl.
*A61F 2/24* (2006.01)
*A61F 2/07* (2013.01)
*A61F 2/86* (2013.01)

(52) U.S. Cl.
CPC ......... *A61F 2/2445* (2013.01); *A61F 2/2403* (2013.01); *A61F 2/2418* (2013.01);
(Continued)

(58) Field of Classification Search
CPC ..... A61F 2/2445; A61F 2/2403; A61F 2/2418
See application file for complete search history.

(56) References Cited

U.S. PATENT DOCUMENTS 3,657,744 A 4/1972 Ersek
4,275,469 A 6/1981 Gabbay
(Continued)

FOREIGN PATENT DOCUMENTS

DE 19857887 A1 7/2000
DE 10121210 A1 11/2002
(Continued)

OTHER PUBLICATIONS

Braido et al., U.S. Appl. No. 29/375,243, filed Sep. 20, 2010, titled "Surgical Stent Assembly".
(Continued)

*Primary Examiner* — Jerrah Edwards
*Assistant Examiner* — Christine L Nelson
(74) *Attorney, Agent, or Firm* — Lerner, David, Littenberg, Krumholz & Mentlik, LLP

(57) ABSTRACT

A prosthetic heart valve includes a collapsible and expandable stent having a proximal end, a distal end, an annulus section adjacent the proximal end and an aortic section adjacent the distal end. The stent is formed of a plurality of struts. A cuff is coupled to the stent. The cuff has one or more features configured to reduce abrasion and/or perivalvular leakage.

15 Claims, 24 Drawing Sheets

Related U.S. Application Data continuation of application No. 13/829,036, filed on Mar. 14, 2013, now Pat. No. 9,326,856.

(52) U.S. Cl.
CPC ............... *A61F 2/07* (2013.01); *A61F 2/2412* (2013.01); *A61F 2/86* (2013.01); *A61F 2220/0075* (2013.01); *A61F 2230/0069* (2013.01); *A61F 2250/0028* (2013.01); *A61F 2250/0036* (2013.01); *A61F 2250/0069* (2013.01)

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,480,423 A | 1/1996 | Ravenscroft et al. |
| 5,693,085 A | 12/1997 | Buirge et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 6,951,573 B1 | 10/2005 | Dilling |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz et al. |
| 7,247,167 B2 | 7/2007 | Gabbay |
| 7,267,686 B2 | 9/2007 | DiMatteo et al. |
| 7,276,078 B2 | 10/2007 | Spenser et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,374,573 B2 | 5/2008 | Gabbay |
| 7,381,218 B2 | 6/2008 | Schreck |
| 7,381,219 B2 | 6/2008 | Salahieh et al. |
| 7,452,371 B2 | 11/2008 | Pavcnik et al. |
| 7,510,572 B2 | 3/2009 | Gabbay |
| 7,510,575 B2 | 3/2009 | Spenser et al. |
| 7,524,331 B2 | 4/2009 | Birdsall |
| 7,534,261 B2 | 5/2009 | Friedman |
| RE40,816 E | 6/2009 | Taylor et al. |
| 7,585,321 B2 | 9/2009 | Cribier |
| 7,628,805 B2 | 12/2009 | Spenser et al. |
| 7,682,390 B2 | 3/2010 | Seguin |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,892,281 B2 | 2/2011 | Seguin et al. |
| 7,914,569 B2 | 3/2011 | Nguyen et al. |
| 7,959,666 B2 | 6/2011 | Salahieh et al. |
| 7,959,672 B2 | 6/2011 | Salahieh et al. |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S | 5/2012 | Braido et al. |
| D660,967 S | 5/2012 | Braido et al. |
| 8,182,528 B2 | 5/2012 | Salahieh et al. |
| 8,221,493 B2 | 7/2012 | Boyle et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| 8,454,686 B2 | 6/2013 | Alkhatib |
| 8,500,798 B2 | 8/2013 | Rowe et al. |
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,685,080 B2 | 4/2014 | White |
| 8,728,154 B2 | 5/2014 | Alkhatib |
| 8,747,459 B2 | 6/2014 | Nguyen et al. |

(56) References Cited

U.S. PATENT DOCUMENTS

| | | |
|---|---|---|
| 8,764,820 B2 | 7/2014 | Dehdashtian et al. |
| 8,795,357 B2 | 8/2014 | Yohanan et al. |
| 8,801,776 B2 | 8/2014 | House et al. |
| 8,808,356 B2 | 8/2014 | Braido et al. |
| 8,828,078 B2 | 9/2014 | Salahieh et al. |
| 8,834,563 B2 | 9/2014 | Righini |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |
| 8,961,595 B2 | 2/2015 | Alkhatib |
| 8,974,523 B2 | 3/2015 | Thill et al. |
| 8,974,524 B2 | 3/2015 | Yeung et al. |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0102837 A1 | 5/2004 | Boyle et al. |
| 2004/0111111 A1 | 6/2004 | Lin |
| 2004/0210304 A1 | 10/2004 | Seguin et al. |
| 2004/0260389 A1 | 12/2004 | Case et al. |
| 2005/0096726 A1 | 5/2005 | Sequin et al. |
| 2005/0137682 A1 | 6/2005 | Justino |
| 2005/0137695 A1 | 6/2005 | Salahieh et al. |
| 2005/0137697 A1 | 6/2005 | Salahieh et al. |
| 2005/0203605 A1 | 9/2005 | Dolan |
| 2005/0256566 A1 | 11/2005 | Gabbay |
| 2006/0008497 A1 | 1/2006 | Gabbay |
| 2006/0020327 A1 | 1/2006 | Lashinski et al. |
| 2006/0025857 A1 | 2/2006 | Bergheim et al. |
| 2006/0036308 A1 | 2/2006 | Goshgarian |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0161249 A1 | 7/2006 | Realyvasquez et al. |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0276027 A1 | 11/2009 | Glynn |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1 | 4/2011 | Braido et al. |
| 2011/0137397 A1* | 6/2011 | Chau ............ A61F 2/2409 623/1.11 |
| 2011/0172765 A1 | 7/2011 | Nguyen et al. |
| 2011/0208283 A1 | 8/2011 | Rust |
| 2011/0264206 A1 | 10/2011 | Tabor |
| 2011/0276129 A1 | 11/2011 | Salahieh et al. |
| 2011/0301700 A1 | 12/2011 | Fish et al. |
| 2011/0319989 A1 | 12/2011 | Lane et al. |
| 2012/0035722 A1 | 2/2012 | Tuval |
| 2012/0071969 A1 | 3/2012 | Li et al. |
| 2012/0078347 A1 | 3/2012 | Braido et al. |
| 2012/0101572 A1 | 4/2012 | Kovalsky et al. |
| 2012/0123529 A1 | 5/2012 | Levi et al. |
| 2012/0197391 A1 | 8/2012 | Alkhatib et al. |
| 2012/0209370 A1 | 8/2012 | Thill et al. |
| 2012/0303116 A1 | 11/2012 | Gorman, III et al. |
| 2013/0274873 A1 | 10/2013 | Delaloye et al. |
| 2014/0000112 A1 | 1/2014 | Braido et al. |
| 2014/0121763 A1 | 5/2014 | Duffy et al. |
| 2014/0155997 A1 | 6/2014 | Braido |
| 2014/0214159 A1 | 7/2014 | Vidlund et al. |
| 2014/0228946 A1 | 8/2014 | Chau et al. |
| 2014/0243969 A1 | 8/2014 | Venkatasubramanian et al. |
| 2014/0303719 A1 | 10/2014 | Cox et al. |
| 2014/0324164 A1 | 10/2014 | Gross et al. |
| 2014/0343671 A1 | 11/2014 | Yohanan et al. |
| 2014/0350668 A1 | 11/2014 | Delaloye et al. |
| 2014/0350669 A1 | 11/2014 | Gillespie et al. |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 2537487 A1 | 12/2012 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |

(56) References Cited

FOREIGN PATENT DOCUMENTS

| WO | 03047468 A1 | 6/2003 |
| --- | --- | --- |
| WO | 06073626 A2 | 7/2006 |
| WO | 2007071436 A2 | 6/2007 |
| WO | 2007081820 A1 | 7/2007 |
| WO | 08070797 A2 | 6/2008 |
| WO | 2009042196 A2 | 4/2009 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |
| WO | 2011051043 A1 | 5/2011 |
| WO | 2012178115 A2 | 12/2012 |
| WO | 2013085719 A1 | 6/2013 |
| WO | 2014163706 A1 | 10/2014 |

OTHER PUBLICATIONS

Buellesfeld, et al., "Treatment of paravalvular leaks through inverventional techniques," Multimed Man Cardiothorac Surg., Department of Cardiology, Ben University Hospital, pp. 1-8, Jan. 2011.
Catheter-implanted prosthetic heart valves, Knudsen, L.L., et al., The International Journal of Artificial Organs, vol. 16, No. 5 1993, pp. 253-262.
De Cicco, et al., "Aortic valve periprosthetic leakage: anatomic observations and surgical results," The Annals of thoracic surgery, vol. 79, No. 5, pp. 1480-1485, May 2005.
Examination Report for EP14711883.0 dated Jul. 27, 2018.
Gössl, et al., "Percutaneous treatment of aortic and mitral valve paravalvular regurgitation," Current Cardiology Reports, vol. 15, No. 8., pp. 1-8, Aug. 2013.
Heat Advisor, "Heart repairs without surgery, Minimally invasive procedures aim to correct valve leakage", Technology Frontier, Sep. 2004, PubMed ID 15586429.
Hourihan, et al., "Transcatheter Umbrella Closure of Valvular and Paravalvular Leaks," Journal of the American College of Cardiology, vol. 20, No. 6, pp. 1371-1377, Nov. 1992.
International Search Report and Written Opinion for Application No. PCT/US2014/019443 dated Oct. 21, 2014.
Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
Muñoz, et al., "Guidance of treatment of perivalvular prosthetic leaks.", Current cardiology reports, 16.430, 6 pages, Jan. 2014.
Partial European Search Report in EP16178855, dated Jan. 31, 2017, 7 pages.
Quaden et al., "Percutaneous aortic valve replacement: resection before implantation", pp. 836-840, European J. of Cardio-thoracic Surgery, 27 (2005).
Rohde, et al., "Resection of Calcified Aortic Heart Leaflets In Vitro by Q-Switched 2 μm Microsecond Laser Radiation", Journal of Cardiac Surgery, 30(2):157-62. Feb. 2015.
Ruiz, Carlos, Overview of PRE-CE Mark Transcatheter Aortic Valve Technologies, Euro PCR, dated May 25, 2010.
Swiatkiewicz, et al., "Percutaneous closure of mitral perivalvular leak," Kardiologia Polska, vol. 67, No. 7, pp. 762-764, Jul. 2009.
Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.
U.S. Appl. No. 29/375,260, filed Sep. 20, 2010.

\* cited by examiner

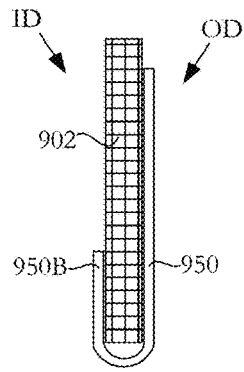
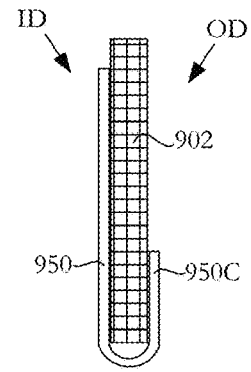
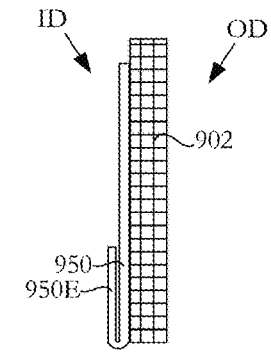
FIG. 9B   FIG. 9C   FIG. 9D   FIG. 9E
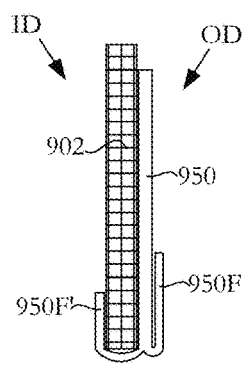
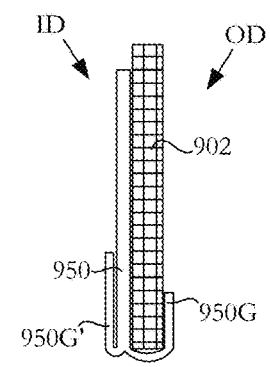
FIG. 9F   FIG. 9G
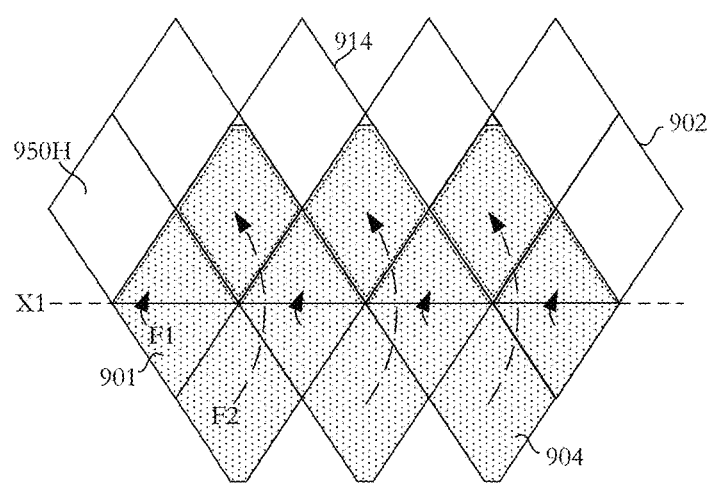
FIG. 9H

CUFF CONFIGURATIONS FOR PROSTHETIC HEART VALVE

CROSS-REFERENCE TO RELATED APPLICATIONS

The present application is a continuation of U.S. patent application Ser. No. 14/745,840, filed Jun. 22, 2015, which is a continuation of U.S. Pat. No. 9,326,856, filed Mar. 14, 2013, the disclosures of which are hereby incorporated herein by reference.

BACKGROUND OF THE INVENTION

The present invention relates to heart valve replacement and, in particular, to collapsible prosthetic heart valves. More particularly, the present invention relates to collapsible prosthetic heart valves having improved cuff attachments.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the valve, assuring its proper location, and then expanding a balloon positioned within the valve stent. For self-expanding valves, on the other hand, the stent automatically expands as the sheath covering the valve is withdrawn.

SUMMARY OF THE INVENTION

In one embodiment, a prosthetic heart valve includes a collapsible and expandable stent having a proximal end, a distal end, an annulus section adjacent the proximal end and an aortic section adjacent the distal end, the stent including a plurality of struts. The heart valve further includes a cuff coupled to a first group of the plurality of struts adjacent a top edge of the cuff and coupled to a second group of the plurality of struts adjacent a bottom edge of the cuff, the top edge being trimmed to closely follow the struts in the first group and the bottom edge being trimmed to closely follow the struts in the second group.

In another embodiment, a prosthetic heart valve includes a collapsible and expandable stent having a proximal end, a distal end, an annulus section adjacent the proximal end and an aortic section adjacent the distal end, the stent including a plurality of struts. The heart valve further includes a collapsible and expandable valve assembly including a cuff and a plurality of leaflets, the plurality of leaflets being coupled to the cuff and the cuff being coupled to selected ones of the plurality of struts via a suture, the cuff being wrapped over one of the plurality of struts to form an outer layer and an inner layer.

In another embodiment, a prosthetic heart valve includes a collapsible and expandable stent having a proximal end, a distal end, an annulus section adjacent the proximal end and an aortic section adjacent the distal end, the stent including a plurality of struts. The heart valve further includes a collapsible and expandable valve assembly including a cuff and a plurality of leaflets, and the cuff being coupled to selected ones of the plurality of struts at suture locations, the cuff having a first thickness in certain regions and a second thickness greater than the first thickness in certain other regions.

In another embodiment, a prosthetic heart valve a collapsible and expandable stent having a proximal end, a distal end, an annulus section adjacent the proximal end and an aortic section adjacent the distal end, the stent including a plurality of struts; The heart valve further includes a collapsible and expandable valve assembly including a cuff and a plurality of leaflets, the cuff being coupled to selected ones of the plurality of struts, the cuff having a plurality of fibers oriented in a manner to adequately distribute stress substantially uniformly throughout the cuff.

In yet another embodiment, a method of determining the relative elastic modulus of a cuff includes applying a predetermined load to the cuff at a location. An amount of deflection of the cuff at the location in response to the predetermined load is measured and the relative modulus of elasticity of the cuff is determined based on the predetermined load and the amount of deflection.

In another embodiment, a prosthetic heart valve includes a collapsible and expandable stent having a proximal end, a distal end, an annulus section adjacent the proximal end and an aortic section adjacent the distal end, the stent including a plurality of struts. The heart valve further includes a collapsible and expandable valve assembly including a cuff and a plurality of leaflets, the cuff being coupled to selected ones of the plurality of struts via a suture, the cuff being formed of a porous material and having microspheres embedded in the porous material, the microspheres being capable of expanding upon contact with blood.

In another embodiment, a prosthetic heart valve includes a collapsible and expandable stent having a proximal end, a distal end, an annulus section adjacent the proximal end and an aortic section adjacent the distal end, the stent including a plurality of struts. The heart valve further includes a collapsible and expandable valve assembly including a cuff and a plurality of leaflets, the cuff being coupled to selected ones of the plurality of struts, the cuff including a first material and a second material, the first material being different from the second material.

In another embodiment, a prosthetic heart valve for implanting within a native valve annulus includes a collapsible and expandable stent having a proximal end, a distal end, an annulus section adjacent the proximal end and an aortic section adjacent the distal end, the stent including a plurality of struts. The heart valve further includes a collapsible and expandable valve assembly including a cuff and a plurality of leaflets, the cuff being coupled to selected ones of the plurality of struts and a buffer including a layer of material coupled to selected regions of the cuff.

In another embodiment, a prosthetic heart valve for implanting within a native valve annulus includes a collapsible and expandable stent having a proximal end, a distal end, an annulus section adjacent the proximal end and an aortic section adjacent the distal end, the stent including a plurality of struts. The heart valve further includes a collapsible and expandable valve assembly including a cuff and a plurality of leaflets, the cuff including a first cuff coupled to select ones of the plurality of struts, the first cuff having extended portions configured to wrap around the proximal end of the stent.

In another embodiment, a prosthetic heart valve for implanting within a native valve annulus includes a collapsible and expandable stent having a proximal end, a distal end, an annulus section adjacent the proximal end and an aortic section adjacent the distal end, the stent including a plurality of struts and hinges interposed between selected struts. The heart valve further includes a collapsible and expandable valve assembly including a cuff and a plurality of leaflets, the cuff being coupled to selected ones of the plurality of struts.

BRIEF DESCRIPTION OF THE DRAWINGS

Various embodiments of the presently disclosed heart valves are disclosed herein with reference to the drawings, wherein:

FIGS. 9B-G are schematic representations of various methods of attaching an extended cuff to a stent;

FIG. 9H is a schematic representation of an extended cuff being folded to both the inner and outer diameters of a stent;

Figure 1:
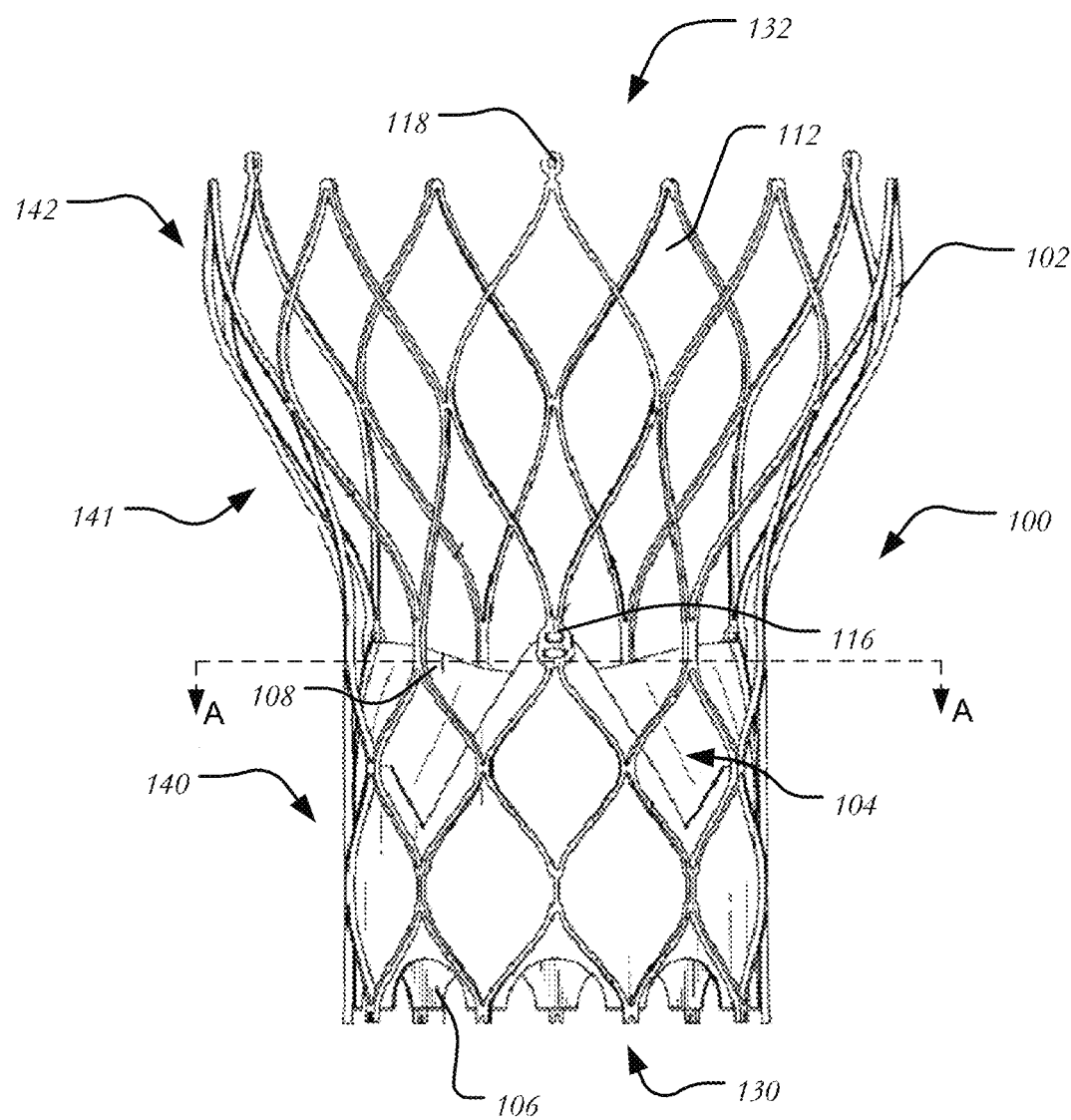
FIG. 1 is a side elevational view of a conventional prosthetic heart valve.

Various embodiments of the present invention will now be described with reference to the appended drawings. It is to be appreciated that these drawings depict only some embodiments of the invention and are therefore not to be considered limiting of its scope.

DETAILED DESCRIPTION OF THE INVENTION

Despite the various improvements that have been made to the collapsible prosthetic heart valve delivery process, conventional devices suffer from some shortcomings. For example, with conventional self-expanding valves, clinical success of the valve is dependent on accurate deployment and sealing. Inaccurate deployment and anchoring may result in the leakage of blood between the implanted heart valve and the native valve annulus, commonly referred to as perivalvular ("also known as paravalvular") leakage. In aortic valves, this leakage enables blood to flow from the aorta back into the left ventricle, reducing cardiac efficiency and putting a greater strain on the heart muscle. Additionally, calcification of the aortic valve may affect performance and the interaction between the implanted valve and the calcified tissue is believed to be relevant to leakage. Additionally, in certain procedures, collapsible valves may be implanted in a native valve annulus without first resecting the native valve leaflets. To reduce these adverse events, the optimal valve would anchor adequately and seal without the need for excessive radial force that could harm nearby anatomy and physiology.

Moreover, anatomical variations from one patient to another may affect wear and durability of portions of a prosthetic heart valve. Specifically, certain portions of a cuff may wear more quickly than others. On the other hand, a thicker cuff may address durability concerns but may unfavorably increase the crimp profile of the prosthetic heart valve, making it difficult to successfully deliver and implant the device. Moreover, removal of a fully-deployed heart valve from the patient may be required if it appears that the valve is not functioning properly due to wear. However, removing a fully deployed heart valve increases the risk of infection and/or damage to heart tissue. Thus, methods and devices are desirable that would reduce the need to remove a prosthetic heart valve from a patient as a result of cuff wear.

There therefore is a need for further improvements to the devices, systems, and methods of manufacturing collapsible prosthetic heart valves, and in particular, self-expanding prosthetic heart valves having cuffs. Among other advantages, the present invention may address one or more of these needs.

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. When used in connection with devices for delivering a prosthetic heart valve or other medical device into a patient, the terms "trailing" and "leading" are to be taken as relative to the user of the delivery devices. "Trailing" is to be understood as relatively close to the user, and "leading" is to be understood as relatively farther away from the user.

FIG. 1 shows one such collapsible stent-supported prosthetic heart valve 100 known in the art. The prosthetic heart valve 100 is designed to replace the function of a native tricuspid, bicuspid or unicuspid valve of a patient, such as a native aortic valve. It should be noted that while the inventions herein are described predominately in connection with their use with a prosthetic aortic valve and a stent having a shape as illustrated in FIG. 1, the inventions may also be used with bicuspid valves, such as the mitral valve, and with stents having different shapes, such as those having a flared or conical annulus section, a less-bulbous aortic section, and the like, and a differently shaped transition section. Examples of collapsible prosthetic heart valves are described in International Patent Application Publication No. WO/2009/042196; U.S. Pat. Nos. 7,018,406; and 7,329,278, the disclosures of all of which are hereby incorporated herein by reference.

Prosthetic heart valve 100 will be described in more detail with reference to FIG. 1. Prosthetic heart valve 100 includes expandable stent 102, which may be formed from biocompatible materials that are capable of self-expansion, such as, for example, shape memory alloys such as nitinol. Stent 102 extends from proximal or annulus end 130 to a distal or aortic end 132, and includes annulus section 140 adjacent the proximal end and aortic section 142 adjacent the distal end. Annulus section 140 has a relatively small cross-section in the expanded condition, while aortic section 142 has a relatively large cross-section in the expanded condition. Preferably, annulus section 140 is in the form of a cylinder having a substantially constant diameter along its length. Transition section 141 may taper outwardly from annulus section 140 to aortic section 142. Each of the sections of stent 102 includes a plurality of cells 112 connected to one another in one or more annular rows around the stent. For example, as shown in FIG. 1, annulus section 140 may have two annular rows of complete cells 112 and aortic section 142 and transition section 141 may each have one or more annular rows of partial cells. Cells 112 in aortic section 142 may be larger than the cells in annulus section 140. The larger cells in aortic section 142 better enable prosthetic valve 100 to be positioned in the native valve annulus without the stent structure interfering with blood flow to the coronary arteries.

Stent 102 may include one or more retaining elements 118 at distal end 132 thereof, the retaining elements being sized and shaped to cooperate with female retaining structures (not shown) provided on the deployment device. The engagement of retaining elements 118 with female retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed. In some variations, retaining elements 118 may be disposed near proximal end 130 of heart valve 100.

Prosthetic heart valve 100 includes valve assembly 104, preferably positioned in the annulus section 140 of stent 102 and secured to the stent. Valve assembly 104 includes cuff 106 and a plurality of leaflets 108, which collectively function as a one-way valve by coapting with one another. As a prosthetic aortic valve, valve 100 has three leaflets 108. However, it will be appreciated that other prosthetic heart valves with which the leak occluders of the present invention may be used may have a greater or lesser number of leaflets.

Although cuff 106 is shown in FIG. 1 as being disposed on the luminal or inner surface of annulus section 140, it is contemplated that the cuff may be disposed on the abluminal or outer surface of the annulus section or may cover all or part of either or both of the luminal and abluminal surfaces. Both cuff 106 and leaflets 108 may be wholly or partly formed of any suitable biological material or polymer such as, for example, PTFE.

Leaflets 108 may be attached along their belly portions to cells 112 of stent 102, with the commissure between adjacent leaflets attached to commissure features 116. As can be seen in FIG. 1, each commissure feature 116 may lie at the intersection of four cells 112 of stent 102, two of the cells being adjacent one another in the same annular row, and the other two cells being in different annular rows and lying in end-to-end relationship. Preferably, commissure features 116 are positioned entirely within the annulus section 140 of stent 102 or at the juncture of annulus section 140 and transition section 141. Commissure features 116 may include one or more eyelets which facilitate the suturing of the leaflet commissure to the stent.

Prosthetic heart valve 100 may be used to replace a native aortic valve, a surgical heart valve, a repair device or a heart valve that has undergone a surgical procedure. The prosthetic heart valve may be delivered to the desired site (e.g., near the native aortic annulus) using any suitable delivery device. During delivery, the prosthetic heart valve is disposed inside the delivery device in the collapsed condition. The delivery device may be introduced into a patient using a transfemoral, transapical, transseptal or any other percutaneous approach. Once the delivery device has reached the target site, the user may deploy prosthetic heart valve 100. Upon deployment, prosthetic heart valve 100 expands so that annulus section 140 is in secure engagement within the native aortic annulus. When the prosthetic heart valve is properly positioned inside the heart, it works as a one-way valve, allowing blood to flow from the left ventricle of the heart to the aorta, and preventing blood from flowing in the opposite direction.

Figure 2:
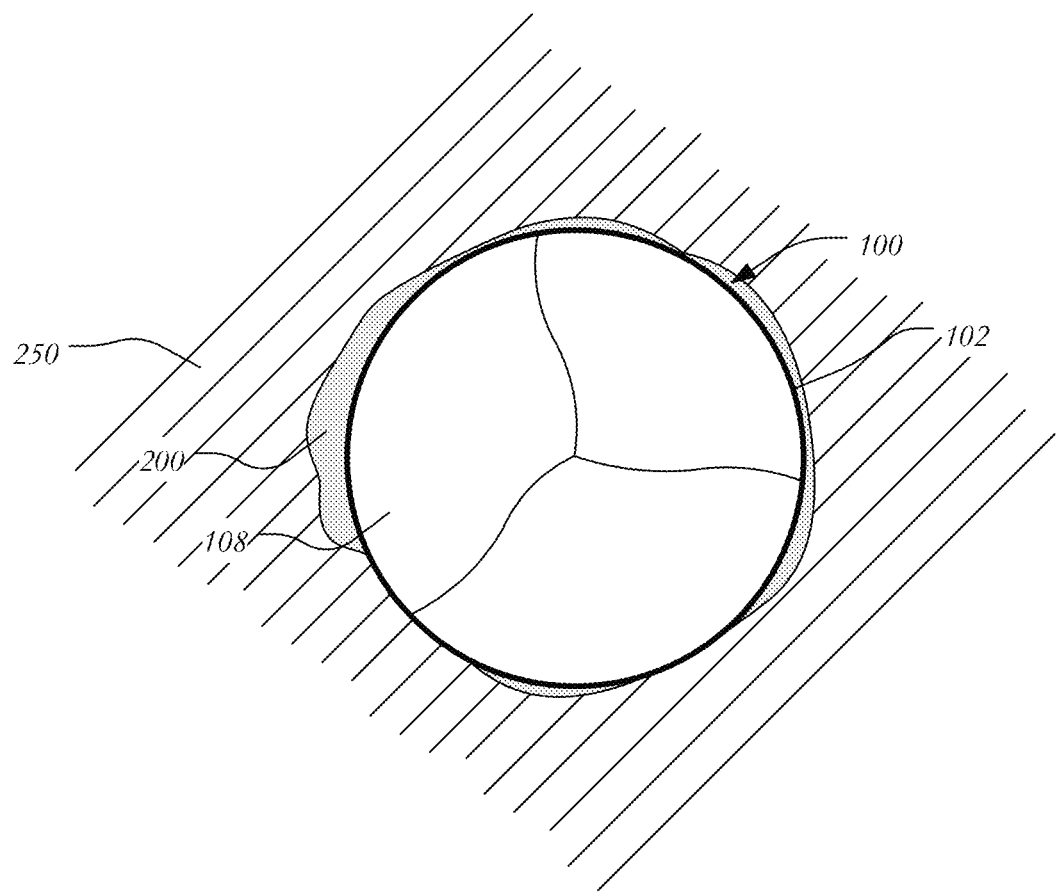
FIG. 2 is a highly schematic cross-sectional view taken along line A-A of FIG. 1 and showing the prosthetic heart valve disposed within a native valve annulus.

FIG. 2 is a highly schematic cross-sectional illustration of prosthetic heart valve 100 disposed within native valve annulus 250. As seen in the figure, the annulus section 140 of stent 102 has a substantially circular cross-section which is disposed within the non-circular native valve annulus 250. At certain locations around the perimeter of heart valve 100, crescent-shaped gaps 200 form between the heart valve and native valve annulus 250. Blood flowing through these gaps and past valve assembly 104 of prosthetic heart valve 100 can cause regurgitation and other inefficiencies which reduce cardiac performance. Such improper fitment may be due to suboptimal native valve annulus geometry due, for example, to calcification of native valve annulus 250 or to unresected native leaflets.

The following embodiments relate to various configurations that address durability and leakage of prosthetic heart valves. Some of the embodiments may be relevant to address durability and crimp profile concerns while others address leakage around the valve assembly through the gaps described above. Still, other embodiments relate to configurations of the cuff that address durability, crimp profile and leakage.

Figure 3A:
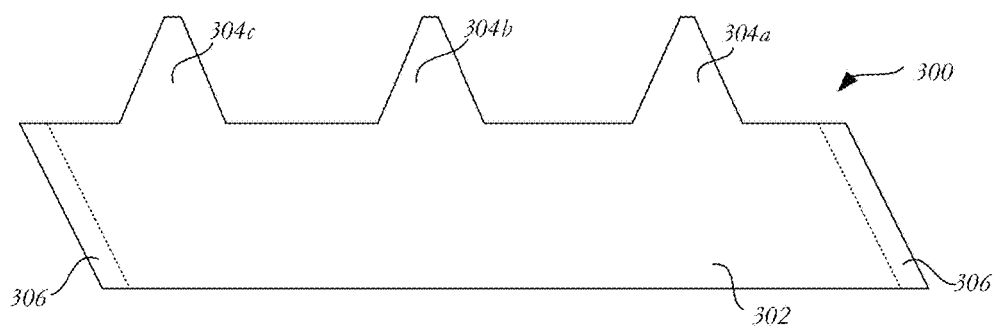
FIG. 3A is a developed view of a cuff.
Figure 3B:
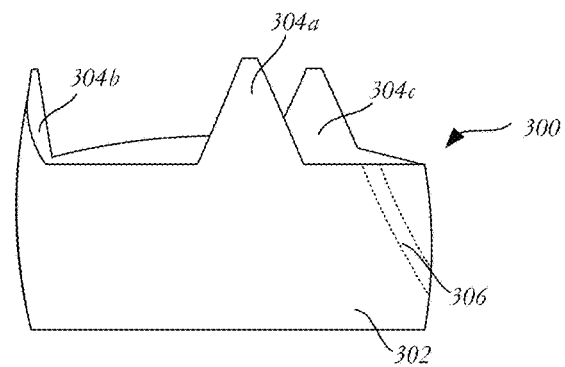
FIG. 3B is a perspective side view of the cuff of FIG. 3A after the attachment portions of the cuff have been coupled together.

FIGS. 3A and 3B illustrate the outer surface of a cuff before coupling to a stent. Cuff 300 includes a body 302, a series of posts 304a, 304b, 304c and a pair of attachment portions 306. Attachment portions 306 are adapted to be coupled together to form cuff 300 into the wrapped or assembled configuration shown in FIG. 3B. Attachment portions 306 may overlap one another and may be coupled together using a suture, an adhesive or any other suitable means. Cuff 300 may be placed in the wrapped configuration either before, during or after being coupled to a stent.

Figure 3C:
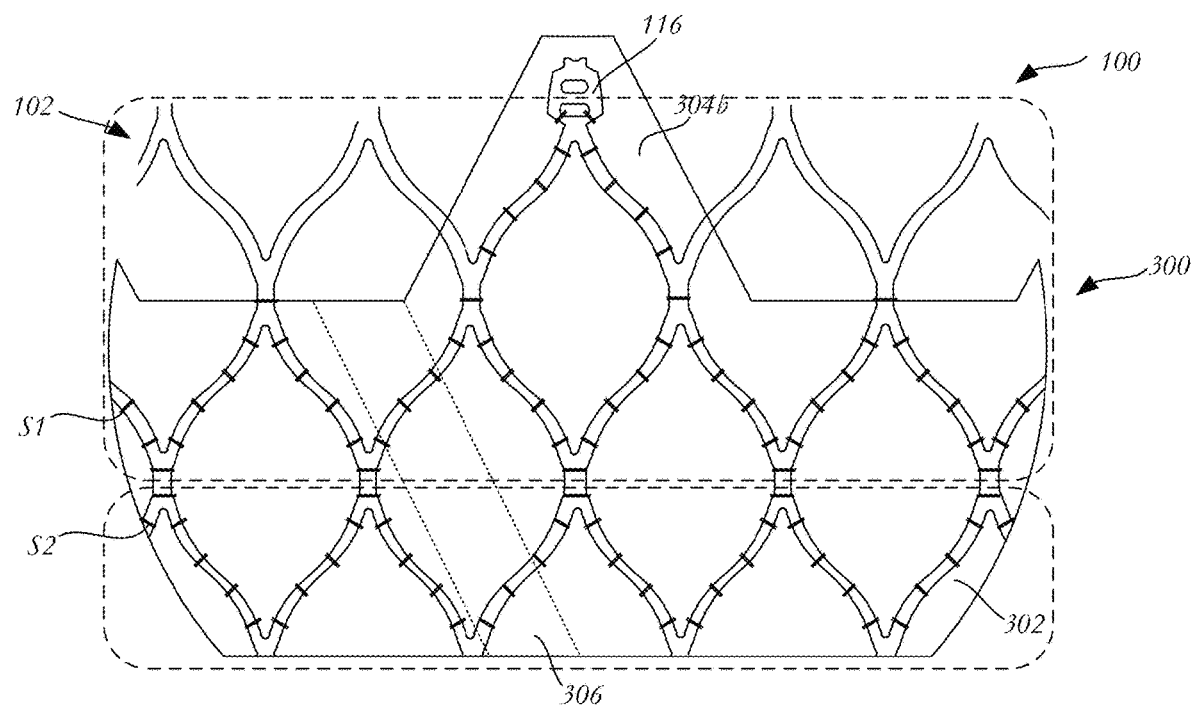
FIG. 3C is a schematic view showing an exemplary arrangement for attaching a cuff to a stent.

FIG. 3C illustrates the coupling of cuff 300 to a portion of stent 102 using sutures. Cuff 300 may be coupled to stent 102 by wrapping sutures S1, S2 along certain struts of the stent 102. Cuff 300 may also be coupled to commissure features 116 along posts 304a, 304b and 304c. While FIG. 3C illustrates cuff 300 disposed on the luminal surface of stent 102, it will be understood that cuff 300 may instead be disposed on the abluminal surface of the stent or on both surfaces. Moreover, while FIG. 3C illustrates the use of two sutures S1, S2 to attach cuff 300 to stent 102, it will be understood that a single suture, or three, four, five, or more sutures may also be used to couple the cuff to the stent.

Excess portions of the body 302 of cuff 300 may be trimmed using a cutting mandrel, a die or other suitable means. A fixation device may be useful in this trimming process. One fixation device useful for this purpose is shown in U.S. Provisional Patent Application Ser. No. 61/666,174 entitled "VALVE ASSEMBLY FOR CRIMP PROFILE" filed Jun. 29, 2012, the content of which is hereby incorporated by reference in its entirety. The trimming of cuff 300 may be accomplished either prior to or after the attachment of the cuff to stent 102. The degree to which excess portions are trimmed from the cuff may affect the valve's performance as will be appreciated from the following series of drawings.

Figure 3D:
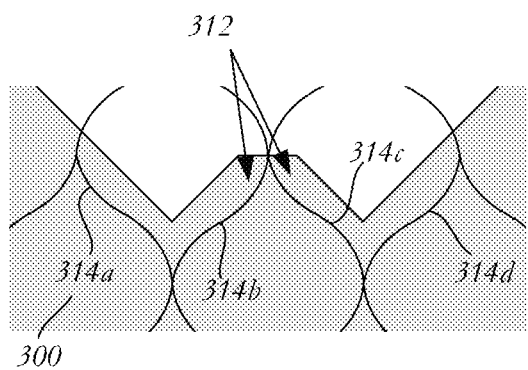
FIGS. 3D and 3E are enlarged side views showing a portion of a first valve having an untrimmed cuff and a portion of a second valve having a trimmed cuff, respectively.
Figure 3E:
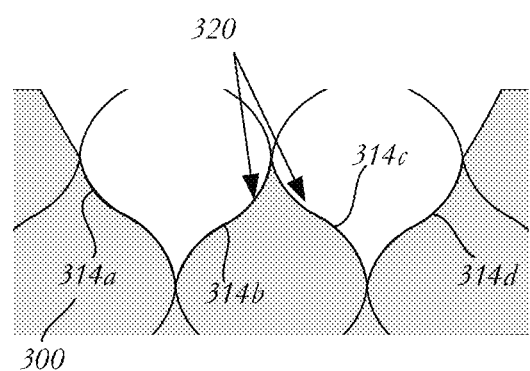

By way of comparison, FIGS. 3D and 3E are partial enlarged drawings of a first stent-cuff assembly that has been coupled without a fixation device and a second stent-cuff assembly that has been coupled using a fixation device, respectively. As seen in FIG. 3D, with cuff 300 coupled to stent 102, the cuff has excess portions 312. Conversely, in FIG. 3E, cuff 300 is coupled to stent 102, but the excess portions 312 have been trimmed away with the aid of a fixation device so that the upper edge of the cuff aligns with struts 314 of the stent. The upper edge 320 of cuff 300 may closely follow struts 314a, 314b, 314c, 314d of stent 102, the upper edge being substantially aligned with the struts. Alternatively, the upper edge 320 of cuff 300 may track the nearest strut, being disposed about 0.5 inches to about 2.0 inches from the nearest strut. With cuff 300 attached to stent 102, leaflets (not shown) may be attached to the cuff to complete the valve assembly.

Figure 3F:
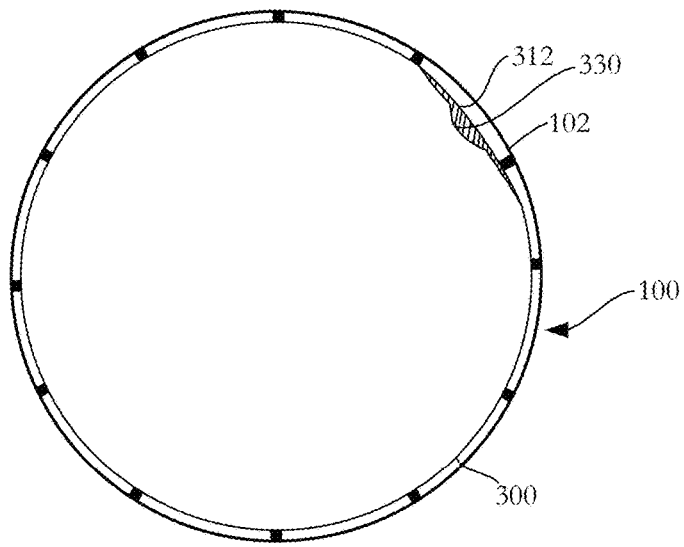
FIGS. 3F and 3G are top views of a valve having an untrimmed cuff and a valve having a trimmed cuff, respectively.
Figure 3G:
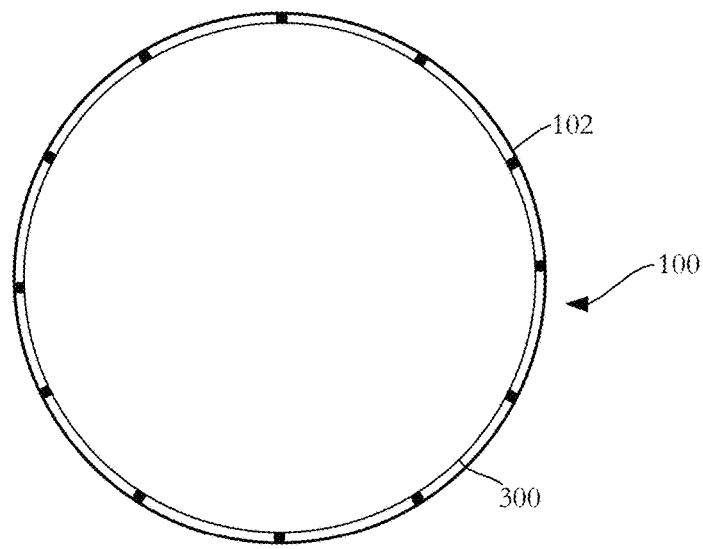

FIG. 3F illustrates an end view of cuff 300 coupled to stent 102. As seen in FIG. 3F, excess portions 312 of cuff 300 have formed a loose segment 330. Loose segment 330 may lead to cuff billowing when the valve is implanted in vivo. In contrast, FIG. 3G illustrates a cuff-stent assembly in which cuff 300 has been trimmed using a fixation device as described above. As seen in FIG. 3G, cuff 300 does not have any loose segments, and is therefore less prone to billowing or swelling. Sufficient tension between the cuff and the stent may provide for superior prosthetic heart valve performance.

Figure 4A:
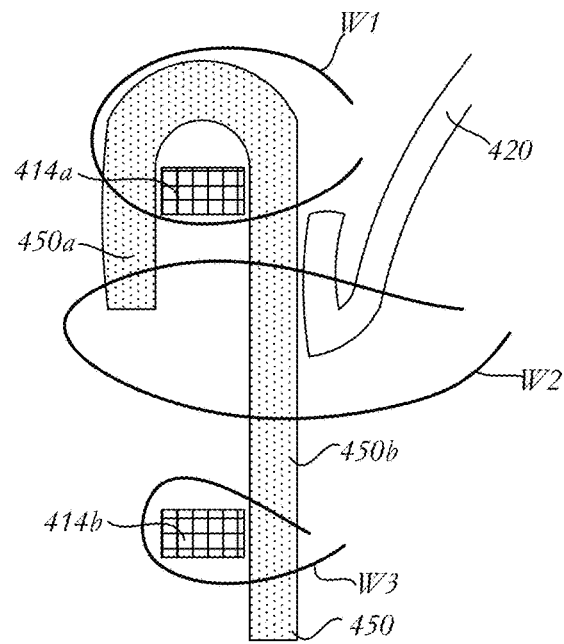
FIGS. 4A and 4B are schematic representations showing the assembly of a cuff, a leaflet and struts of a stent.

FIG. 4A illustrates one method of coupling a cuff 450 to the struts of a stent. Cuff 450 may be coupled to the stent via a single suture or a plurality of sutures. The method illustrated in FIG. 4A utilizes three suture wraps W1, W2, W3 to couple cuff 450 to struts 414a, 414b and leaflet 420. The cuff 450 may be folded over strut 414a and a first suture W1 may wrap around the top of cuff 450, pierce through an outer layer 450a of the cuff, run under strut 414a and then pierce through inner layer 450b of the same cuff, thereby attaching the two layers 450a, 450b of the cuff to strut 414a. A second suture W2 may pierce through two layers of leaflet 420, the inner layer 450b of the cuff, the outer layer 450a of the cuff and loop back around, piercing through the inner layer 450b of the cuff again near a midportion of the cuff, thereby attaching leaflet 420 to the two layers of the cuff. A third suture W3 may pierce through inner layer 450b, wrap around second strut 414b, and pierce inner layer 450b a second time to create a loop, coupling inner layer 450b of the cuff to strut 414b. This configuration may help to protect leaflet 420 from strut 414a.

Figure 4B:
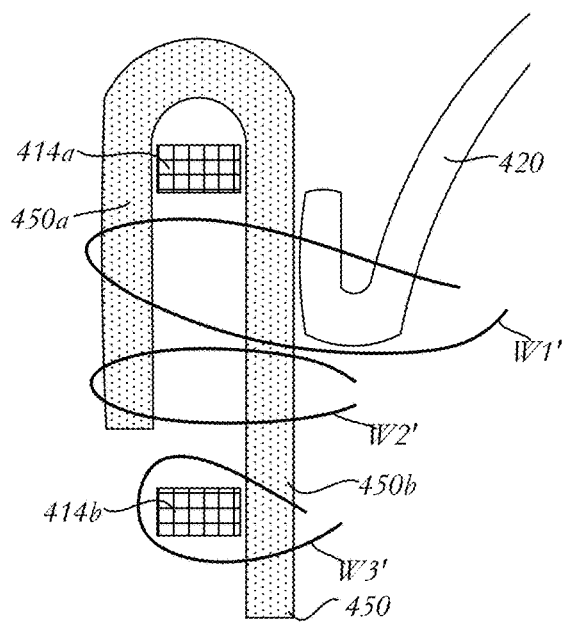

FIG. 4B illustrates a second method of coupling a cuff 450 to the struts of a stent. The method illustrated in FIG. 4B also utilizes three suture wraps W1', W2', W3' to couple cuff 450 to struts 414a, 414b and leaflet 420. The cuff 450 may be folded over strut 414a and a first suture W1' may pierce through two layers of leaflet 420, the inner layer 450b of the cuff, the outer layer 450a of the cuff and return toward the interior of the valve by piercing both the outer layer 450a and the inner layer 450b a second time. A second suture W2' may pierce through the inner layer 450b and outer layer 450a of the cuff in a first direction near the midpoint of the cuff, and then loop back around, piercing through the outer layer 450a and the inner layer 450b in the opposite direction. A third suture W3' may pierce through inner layer 450b, wrap around second strut 414b, and pierce inner layer 450b a second time to create a loop, coupling inner layer 450b to strut 414b as in the first method. It will be understood that variations of these suture patterns are possible and that combinations of the different suture wraps of FIGS. 4A and 4B may also be desirable.

Figure 5A:
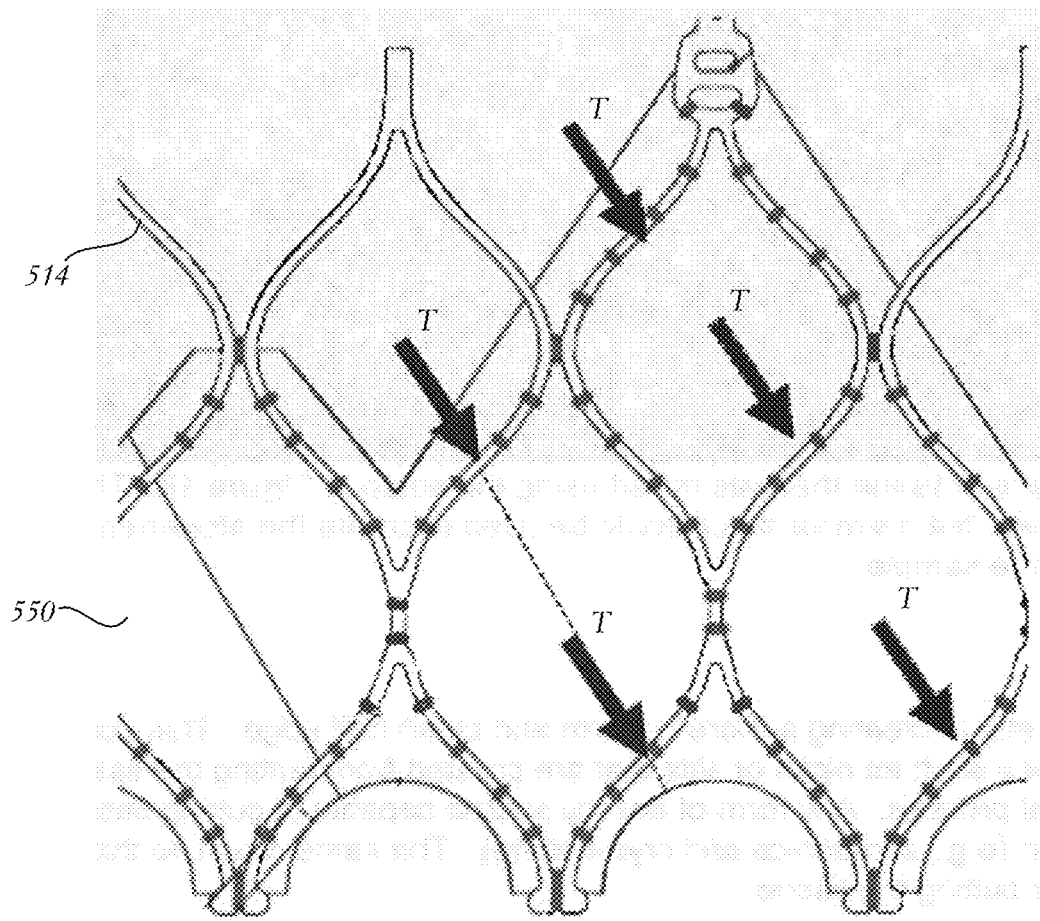
FIG. 5A is an enlarged elevational view of a cuff coupled to struts, the thickness of the cuff differing from one area to another.

In addition to trimming away excess portions of the cuff and using novel suture patterns to improve valve performance, the thickness of the cuff may also be tailored to provide superior heart valve performance. In that regard, a thinning process may be used to create a cuff that has a varying or non-uniform thickness. For example, thinning may be accomplished by cryocutting, ultrasonic cutting, laser ablation and other known techniques. The same technique used to cut the edges of the cuff may be used to control the cuff thickness. FIG. 5A illustrates a cuff 550 coupled to struts 514, the thickness of the cuff being different in some areas than in others. Specifically, thicker portions of cuff 550, as marked by arrows "T", may coincide with suture locations or high stress areas of interest. Cuff 550 may also have areas of reduced thickness to help reduce the crimp profile of the valve. The thickness of cuff 550 may vary so that a technician or user is able to align the cuff with struts 514 by examining the cuff visually. Cuff 550 may also be thickened near the commissure feature attachments as well as near cuff-leaflet junctions (not shown).

Figure 5B:
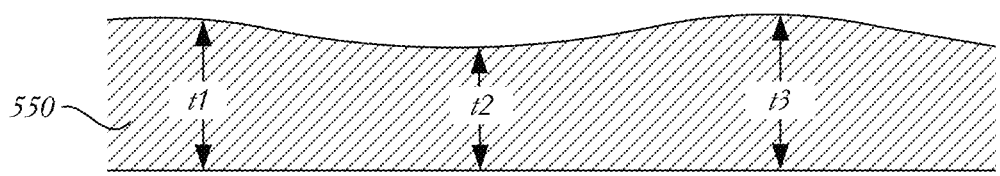
FIG. 5B is a cross-sectional representation of the cuff having a varying thickness.

FIG. 5B illustrates a partial cross-section of cuff 550. As seen in FIG. 5B, cuff 550 may have a variety of thicknesses, with thicker areas such as t1 and t3 being more suitable for suturing and greater load bearing, and thinner areas such as t2 having a smaller profile and more flexibility.

The material of a cuff may also be selected to achieve different goals. In at least some examples, the cuff may be made of a synthetic material such as polyester or ultra high molecular weight polyethylene (UHMWPE) or a suitable combination. Such synthetic materials may enable a thinner cuff to be produced, resulting in a lower crimp profile as well as the need for less force for loading and resheathing. The use of synthetic materials may also increase the durability and life expectancy of the cuff. Fabric and other synthetic materials may further provide adequate biological responses, such as in-growth to reduce PV-leak. Alternatively, the cuff may be formed from natural materials, including porcine, bovine, equine, ovine and kangaroo tissue. Such natural materials may provide acceptable operation and good biological responses.

Figure 5C:
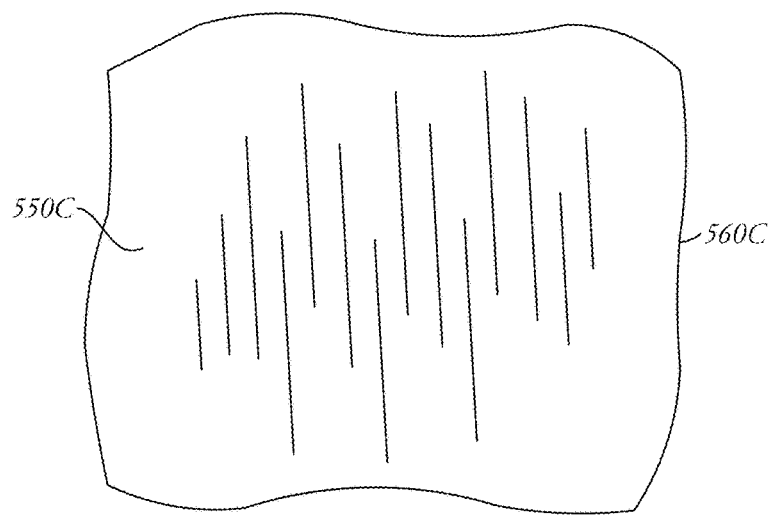
FIGS. 5C and 5D are enlarged views showing portions of a cuff having different fiber orientations.
Figure 5D:
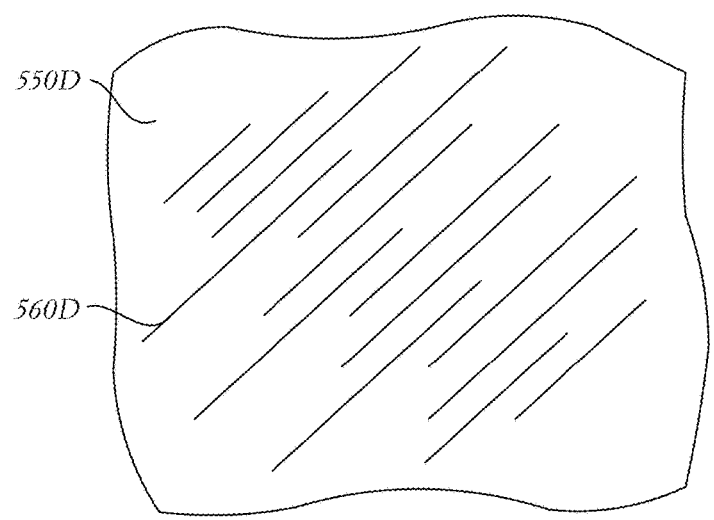

When natural materials are used to form a cuff (e.g., tissue cuffs), the tissue may be oriented in different ways to improve performance. For example, the orientation of tissue fibers may be characterized as circumferential, axial or random and these orientations may be employed in various ways to improve durability or manufacturability, or to provide a number of other benefits. FIGS. 5C and 5D illustrate two tissue portions used for forming a cuff. FIG. 5C illustrates tissue portion 550C in which the tissue fibers 560C are predominantly oriented in a substantially longitudinal direction, i.e., a direction that, when the cuff is assembled to a prosthetic valve, is substantially parallel to the longitudinal axis of the valve. FIG. 5D illustrates tissue portion 550D in which the tissue fibers 560D are predominantly oriented diagonally, i.e., in a direction that is oblique to the longitudinal axis of the prosthetic valve when the cuff is assembled therein. In some examples, tissue fibers 560D may be oriented at a 45 degree angle. Various methods, such as polarized light microscopy, deflection testing and/or tensioning, may be used to determine the dominant tissue fiber orientation. Having characterized the tissue, the cuff may be cut or formed in a manner to best distribute stresses more uniformly throughout the cuff, thus helping to increase the strength and durability of the cuff.

Figure 5E:
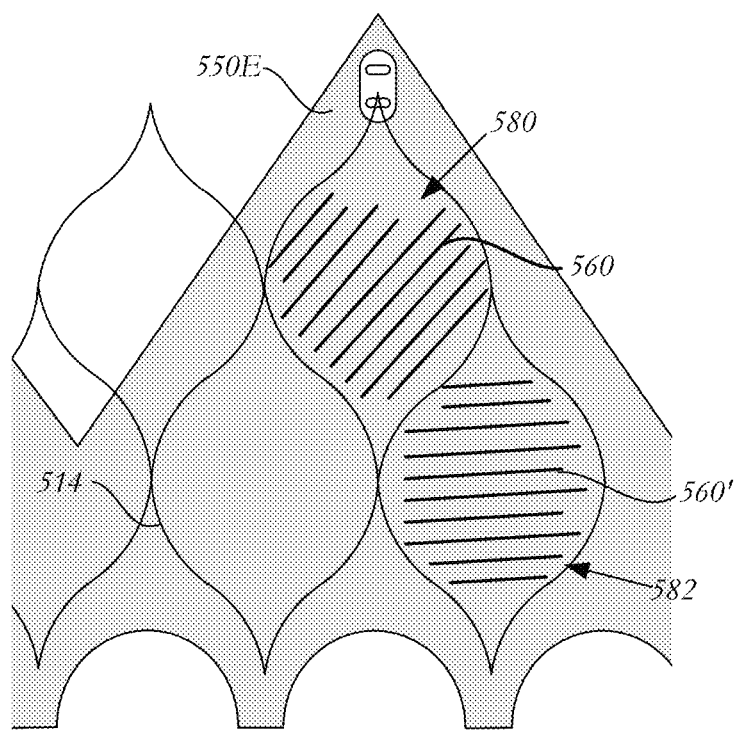
FIG. 5E is an enlarged partial elevational view showing one possible technique of attaching the cuff to the stent based on fiber orientation.

FIG. 5E is a partial view of a valve assembly having a cuff 550E coupled to struts 514. Tissue fibers 560 may be oriented predominantly in a first direction in a first area 580 of the cuff and tissue fibers 560' may be oriented predominantly in a second direction in a second area 582 of the cuff. Specifically, as seen in FIG. 5E, the first area 580 includes a substantially diagonal orientation of tissue fibers 560 while the second area 582 includes a substantially circumferential orientation of tissue fibers 560'. Thus, cuff 550E may be cut and assembled in a manner such that the dominant fiber orientation is in a certain direction or cuff 550E may be formed of multiple pieces of tissue connected together, with each piece being selected to have a specific fiber orientation.

Figure 5F:
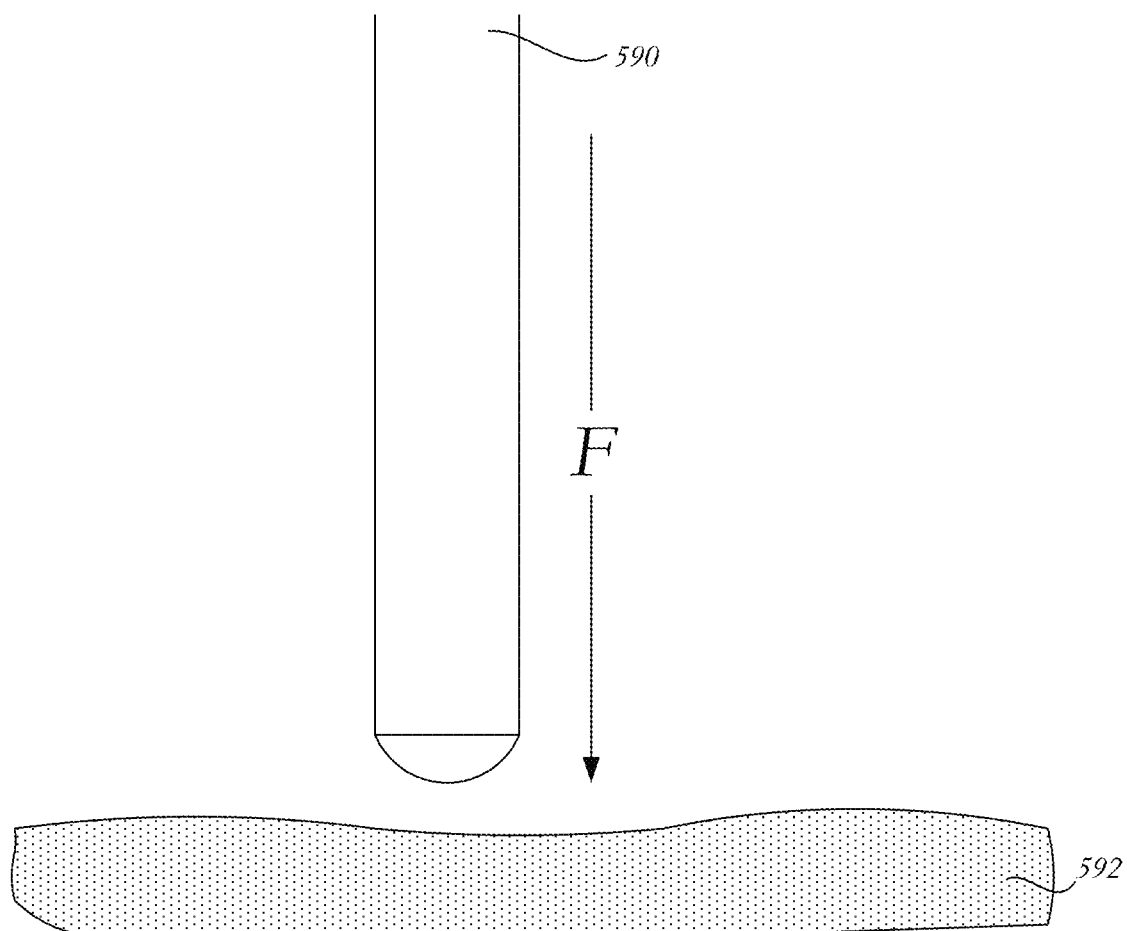
FIG. 5F is a schematic representation of a method of determining the relative elastic modulus of a cuff.

In addition to fiber orientation, the relative elastic modulus of a tissue sample may be examined to determine the suitability of the tissue for use in producing a cuff. One method of calculating the relative elastic modulus will be described with reference to FIG. 5F. A predetermined load 590 may be applied to a tissue sample 592 in the direction of arrow F at one or more locations and the amount of deflection of the tissue sample in response to the load may be measured. The relative modulus of elasticity of the sample may then be calculated based on the amount of deflection and the load. A tissue sample 592 thus may be accepted or rejected based on the calculated modulus or the minimum-maximum deflection of the sample. In at least some examples, the deflection of an acceptable tissue sample 592 is between about 1.0 mm and about 7.0 mm at a load that is physiologically relevant and non-destructive. In at least some other examples, the deflection of an acceptable tissue sample 592 is between about 2.0 mm and about 5.5 mm.

Figure 5G:
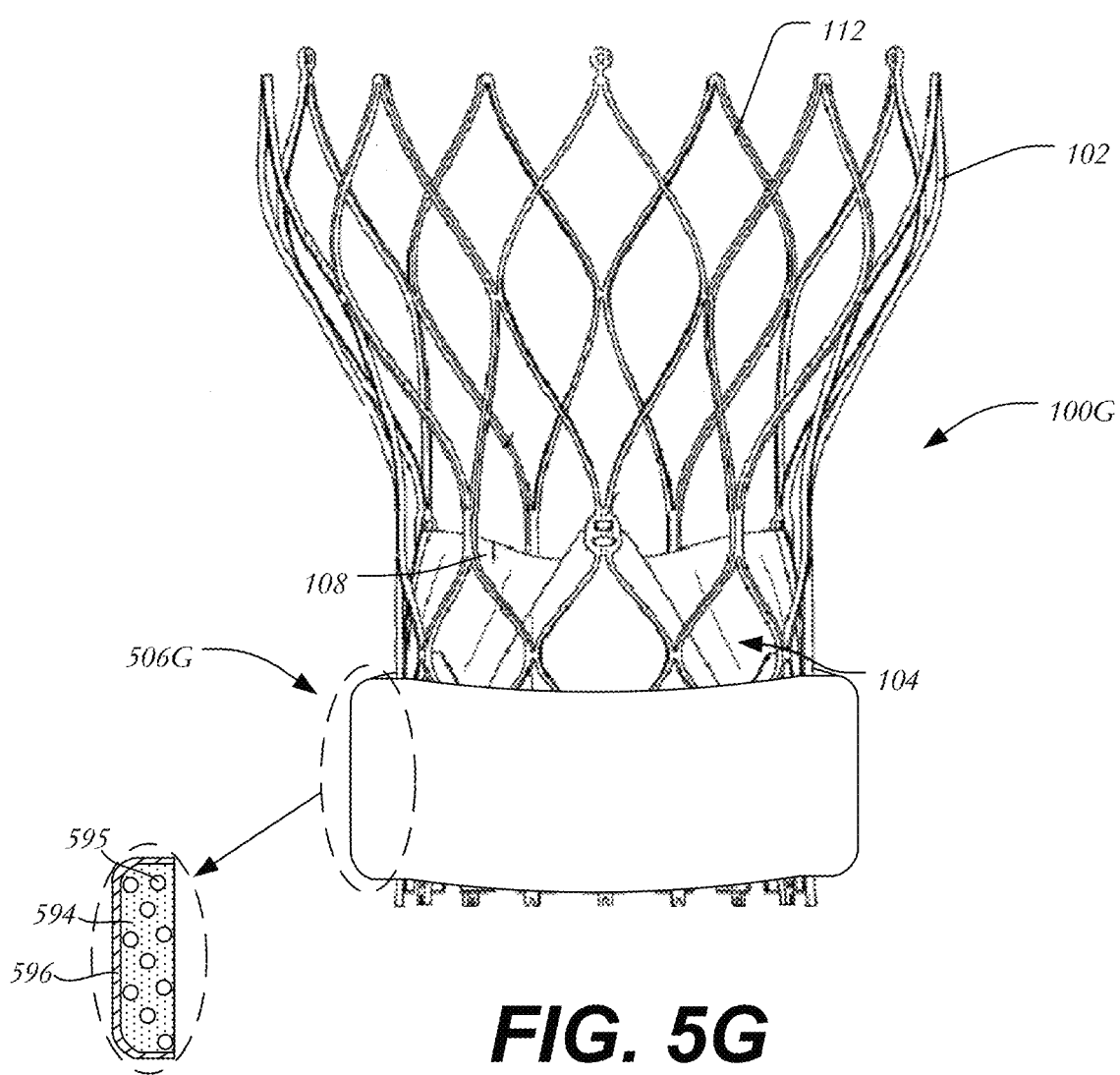
FIG. 5G is a side elevational view of a prosthetic heart valve having an external cuff, with a cross-section of the cuff showing microspheres embedded therein.

Additional features may be added to the cuff to aid in perivalvular leakage. For example, one method of minimizing perivalvular leakage is to incorporate polyvinyl alcohol (PVA), foam shape memory portions, or a sponge-like portion into the material of the cuff. FIG. 5G illustrates a prosthetic heart valve 100G having a stent 102 to which an external cuff 506G is coupled. External cuff 506G may be formed from a porous membrane 594 embedded with microspheres 595. In one example, microspheres 595 may be formed of a dry polyvinyl alcohol sodium acrylate. The individual pores of membrane 594 may be smaller than the microspheres 595 so that the microspheres are retained, but large enough to allow liquid (e.g., blood) to travel therethrough. An optional protective layer 596 may overlie membrane 594 during shipping and storage of hydrated tissue valves, but may be omitted for dry valves. As cuff 506G contacts blood upon the implantation of prosthetic heart valve 100G, microspheres 595 may swell in size, increasing the size and specifically the diameter of the cuff. The enlarged cuff thus fills the gaps between the native valve annulus and the prosthetic heart valve, minimizing or preventing perivalvular leakage.

In addition to reducing perivalvular leakage, polyvinyl alcohol (PVA) granules may be added to the cuff and/or the leaflets in prosthetic heart valves featuring all dry components (e.g., dry tissue technology or all fabric cuff/leaflet designs) instead of a storage solution. Prosthetic heart valves having PVA granules may be stored, shipped and loaded into a delivery device dry without activating the PVA. The PVA will be activated when the valve contacts blood upon deployment. Such a technique may be considered advantageous over other techniques which use a storage solution as the storage solution may prematurely activate the PVA, thereby reducing its effectiveness in mitigating valve leakage at implantation.

Figure 6A:
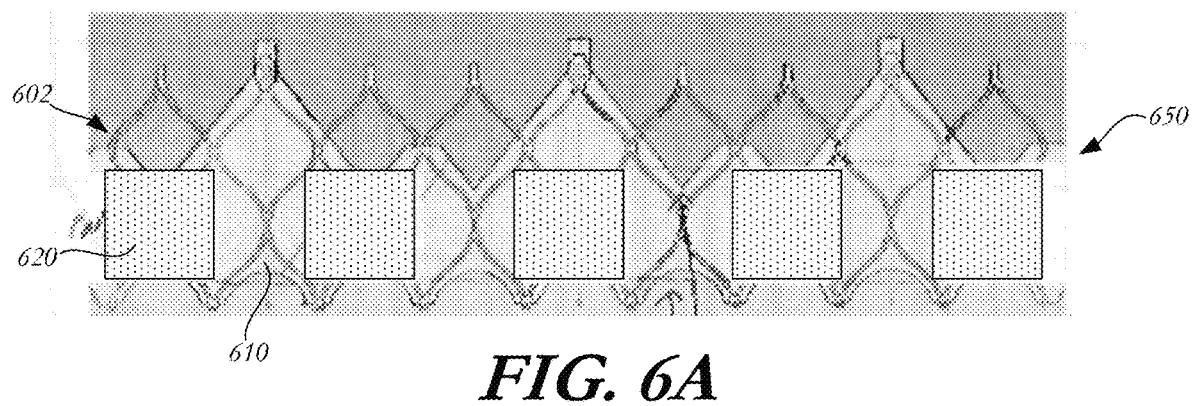
FIG. 6A is a developed view of a portion of a valve having a cuff with a combination of synthetic portions and tissue portions.

In addition to using entirely natural materials or entirely synthetic materials, the cuff may be formed from a combination of natural and synthetic materials. FIG. 6A illustrates an example of a fabric-tissue combination cuff 650. In one arrangement, cuff 650 may include bands or strips of synthetic fabric 620 coupled to a base tissue material 610. Fabric 620 may be woven to tissue material 610 and/or stent 602 and may increase the strength of cuff 650 and help distribute the load evenly across the valve assembly. In an alternate arrangement, cuff 650 may be formed of alternating portions of natural and synthetic materials. The combination cuff may also be formed with the two materials reversed (e.g., a base of fabric overlaid with strips of tissue). By combining tissue and fabric, the crimping profile and rigidity of the cuff may be adjusted as desired. In at least some other examples, a single cell, a row of cells or other desired grouping of cells may include natural material, synthetic materials or a combination of both.

Figure 6B:
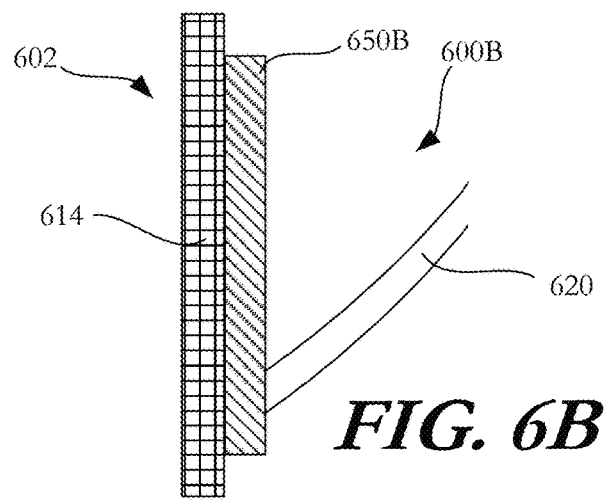
FIGS. 6B-D are schematic representations showing various arrangements for coupling a leaflet and cuff to a stent to form a prosthetic heart valve.
Figure 6C:
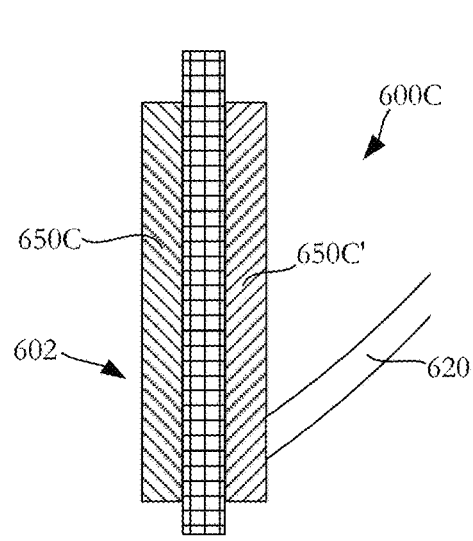
Figure 6D:
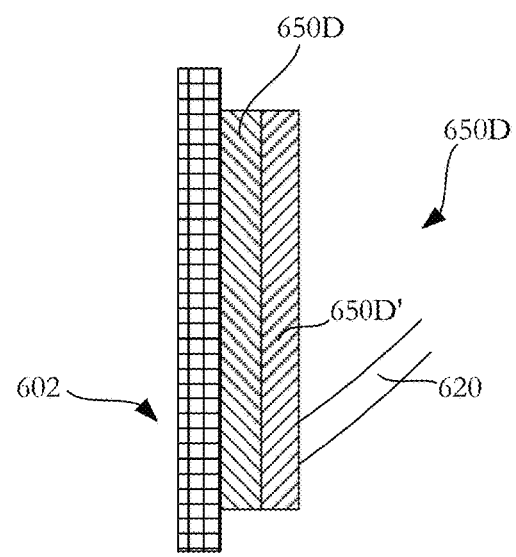

FIGS. 6B-D illustrate various configurations for coupling a leaflet and a cuff to a stent to form a prosthetic heart valve. FIG. 6B illustrates the use of a single-layer cuff. In this configuration of prosthetic heart valve 600B, a cuff 650B may be coupled to struts 614 on the luminal surface of stent 602, with leaflet 620 being coupled to cuff 650B.

FIG. 6C illustrates a prosthetic heart valve 600C having a cuff including a first layer 650C and a second layer 650C.

The first layer 650C may be coupled to the abluminal surface of stent 602 and may be made of tissue or a fabric. The second layer 650C' may be coupled to the luminal surface of stent 602, the stent effectively being sandwiched between the two layers 650C, 650C'. The second layer 650C' may be formed of the same or a different material than the first layer 650C. Leaflet 620 may be coupled to the second layer 650C' as seen in FIG. 6C.

FIG. 6D illustrates a second variation of a prosthetic heart valve 600D having a cuff including a first layer 650D and a second layer 650D'. In this example, both cuff layers 650D, 650D' are disposed on the luminal surface of stent 602, the first layer 650D being coupled to the stent and the second layer 650D' being coupled to the first layer 650D. The first layer 650D and the second layer 650D' may be formed of the same or different materials. Leaflet 620 may be coupled to the second layer 650D'. It will be understood that various techniques may be used to couple the layers 650D, 650D' to one another or to stent 602. For example, sutures, staples, an adhesive, ultrasonic welding and the like may be used to couple or bond the layers of the cuff together. Thus, the inclusion of a second layer in the cuff may improve performance and increase the durability of the cuff.

Figure 7A:
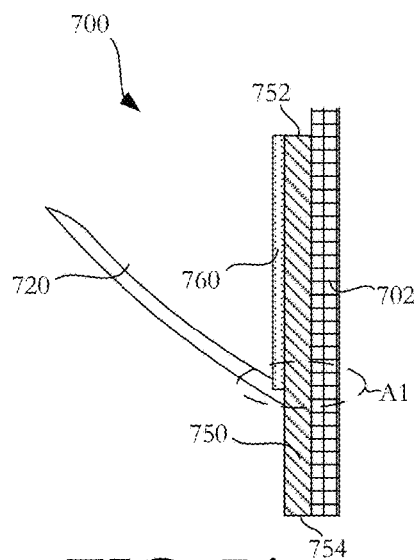
FIGS. 7A and 7B are schematic representations showing the attachment of a cuff, a leaflet and a buffer to a stent.

In another embodiment, instead of forming the cuff with two layers, a buffer material may be disposed over a portion of the cuff. As seen in FIG. 7A, a prosthetic heart valve 700 may include a stent 702 and a cuff 750 disposed over a portion of the stent. Cuff 750 may include any of the materials discussed above, such as fabric or other synthetic materials, or natural materials, such as tissue, and may extend between a first edge 752 at the outflow end of the cuff and a second edge 754 substantially aligned with the bottom of stent 702. A buffer layer 760 disposed over a portion of cuff 750 may be coupled to the cuff. In order to reduce crimp profile, buffer 760 may align with the first edge 752 of cuff 750 as shown in FIG. 7A and extend over only a portion of the cuff (e.g., buffer 760 may terminate prior to the second edge 754 of the cuff).

Figure 7B:
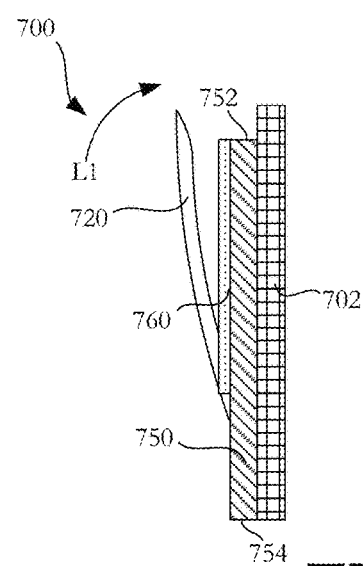

Buffer 760 may be made of a non-porous, non-abrasive material such as, for example, thin porcine pericardium. In at least some examples, buffer 760 is non-load bearing and the material may be selected to be thin and lubricious with minimal to no porosity. Examples of materials from which buffer 760 may be formed include thin porcine pericardium, ultra-high molecular weight polyethylene (UHMWPE), polytetrafluoroethylene (PTE) membrane or other suitable polymers. Additionally, buffer 760 may be made of a fiber material having a hydrophilic coating to offer increased lubricity, for example, to reduce the forces required to load or resheath the prosthetic heart valve. The hydrophilic coating may also help mitigate perivalvular leakage. Specifically, after implantation, the hydrophilic coating may participate in dynamic hydrogen bonding after contact with blood, thus forming additional material volume around the fibers to help reduce the potential for leakage. Leaflets 720 may be attached to cuff 750, to buffer 760 or to both cuff 750 and buffer 760 in region A1. As seen in FIG. 7B, when leaflet 720 opens under pressure in the direction of arrow L1, it may press against buffer 760 instead of cuff 750, thereby reducing the risk of abrasion to both the cuff and leaflet. Attachment techniques for coupling the cuff to the buffer will be described in greater detail below.

Figure 7C:
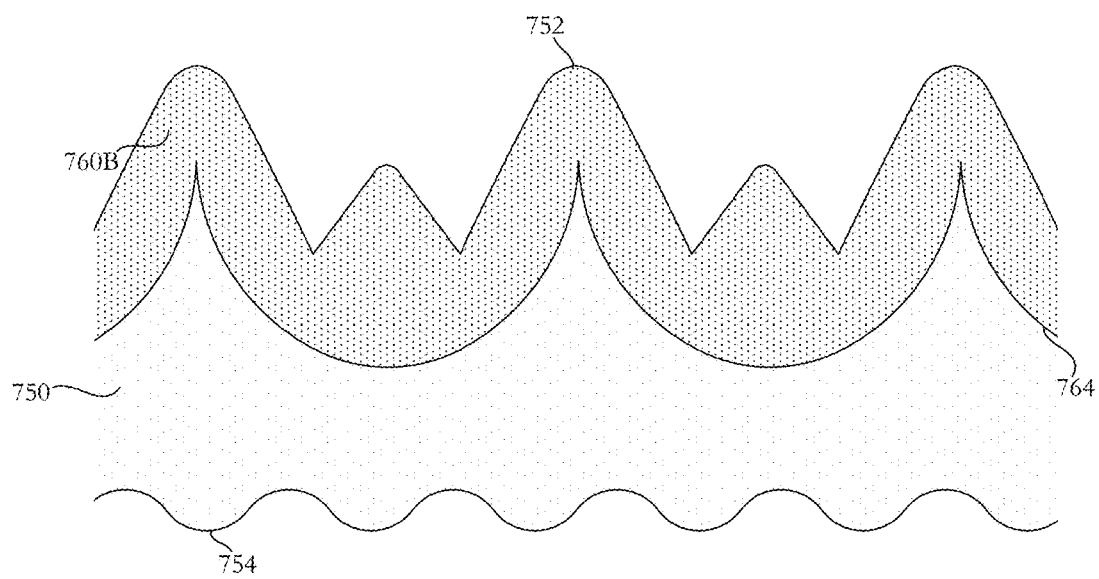
FIGS. 7C-G are schematic representations showing various cuff and buffer arrangements.

FIG. 7C illustrates one possible configuration of the buffer. In this configuration, buffer 760C may follow the contours of cuff 750 near the first edge 752 of the cuff and form a parabolic pattern 764 halfway between the first edge 752 and the second edge 754 of the cuff. Parabolic pattern 764 may follow the contours of the attachment of a leaflet belly (not shown) to the cuff. Buffer 760C may be first coupled to cuff 750 and the parabolic pattern 764 of the buffer may serve as a guide for attaching the leaflet belly to the cuff to provide a repeatable attachment, thereby improving valve function. As illustrated, buffer 760C is formed of a single piece of natural or synthetic material. It will be understood, however, that the buffer may be formed of multiple pieces of natural or synthetic materials connected to one another.

Figure 7D:
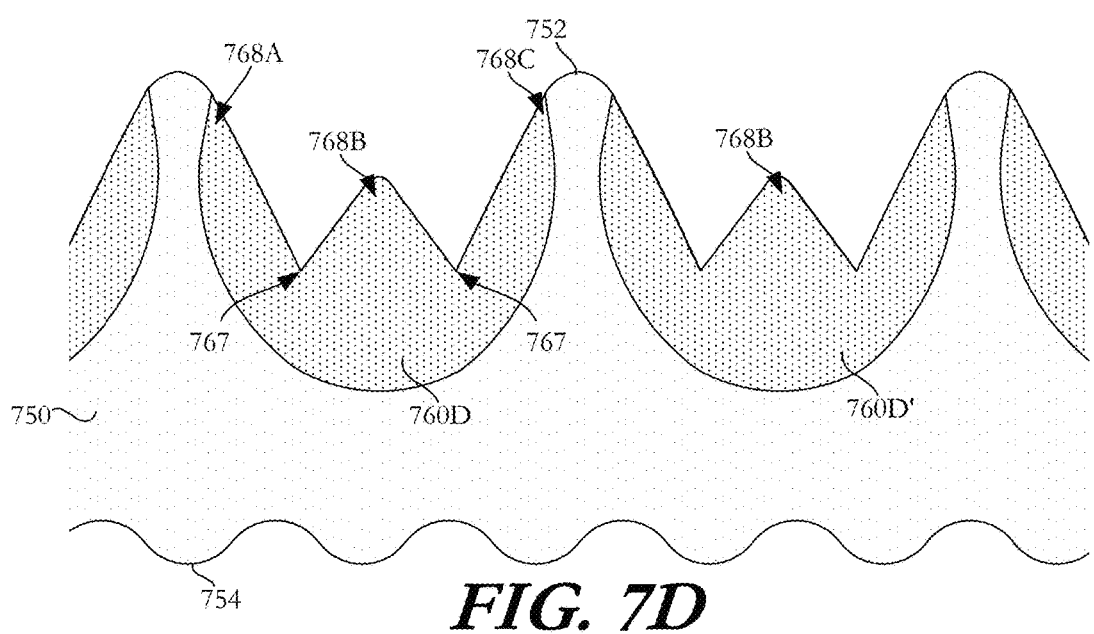

FIG. 7D illustrates a cuff-buffer assembly in which the buffer is formed of multiple pieces of fabric. Each segment 760D of the buffer may follow at least a portion of the first edge 752 of cuff 750 and may include one or more peaks 768 disposed adjacent commissure features (not shown) and between a plurality of valleys 767. Each segment 760D of the buffer may include a generally W-shaped profile including three peaks 768A, 768B, 768C and two valleys 767. The use of multiple buffer segments 760D, 760D', etc. may serve to further reduce the material used in the prosthetic heart valve and thus reduce the overall crimp profile of the assembled device.

Figure 7E:
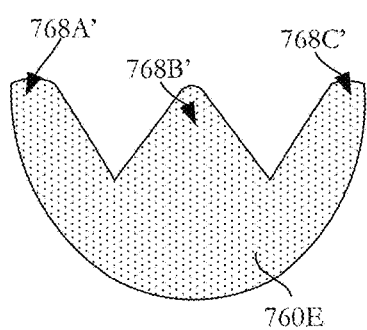
Figure 7F:
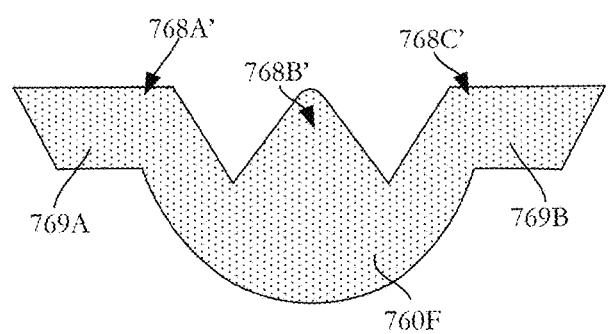

FIGS. 7E and 7F illustrate two more configurations of buffer. In FIG. 7E, buffer 760E includes three peaks 768A', 768B', 768C' that are all of the same height. In this example, the two end peaks 768A', 768C' do not extend all the way up toward the commissure feature, but terminate at the same height as middle peak 768B'. In FIG. 7F, buffer 760F is similar to that of FIG. 7E, but includes additional flaring portions 769A, 769B connected to peaks 768A' and 768C' to provide additional leakage mitigation.

Figure 7G:
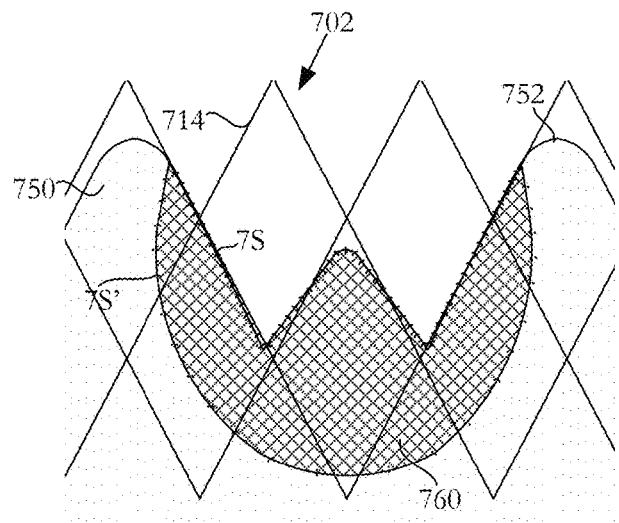

The attachment of a buffer to cuff 750 and/or select struts of the stent may depend on the shape and profile of the buffer. One example of such an attachment is shown in FIG. 7G, which shows an exemplary attachment of a segment 760D of the buffer of FIG. 7D. Buffer segment 760D may be sutured along first edge 752 of cuff 750 with the same sutures 7S that attach the cuff to the struts 714 of stent 702. The bottom edge of buffer segment 760D may be attached to cuff 750, struts 714, and/or a valve leaflet (not shown) via the sutures 7S' that attach the leaflet belly to the cuff.

FIGS. 7H-K illustrate several configurations for suturing a cuff and a buffer to struts 714. Specifically, these figures illustrate several configurations of the sutures 7S along first edge 752 shown in FIG. 7G.

Figure 7H:
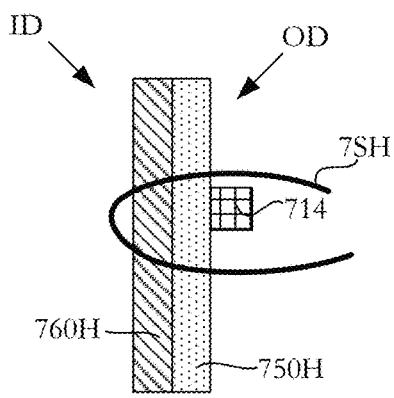
FIGS. 7H-K are schematic representations showing the attachment of a cuff and a buffer to a stent.

In one configuration shown in FIG. 7H, suture 7SH runs from the outer diameter OD of the assembly, over strut 714, and through cuff 750H and buffer 760H to the inner diameter ID, and then from the inner diameter back through buffer 760H and cuff 750H to the outer diameter while passing under strut 714.

Figure 7I:
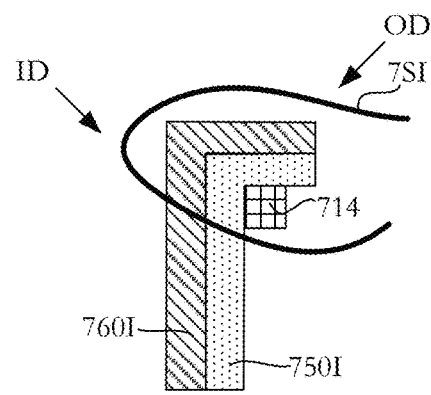

In another configuration shown in FIG. 7I, the upper edges of cuff 750I and buffer 760I are bent over strut 714 and suture 7SI is passed from the outer diameter OD over both upper edges and strut 714 to the inner diameter ID, and then from the inner diameter back through buffer 760I and cuff 750I to the outer diameter at a position below strut 714.

Figure 7J:
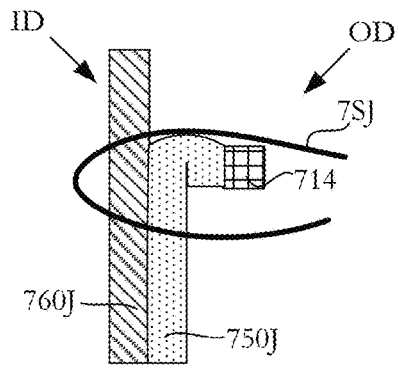

In FIG. 7J, cuff 750J is doubled over itself at the axial location of strut 714 and suture 7SJ is passed from the outer diameter OD over strut 714 and both layers of cuff 750J, through buffer 760J to the inner diameter ID, and then from the inner diameter back through buffer 760J and cuff 750J to the outer diameter at a position below strut 714.

Figure 7K:
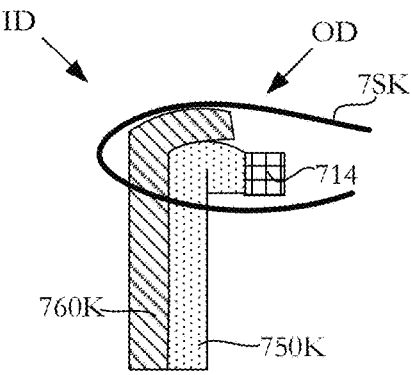

In yet another configuration shown in FIG. 7K, cuff 750K may be doubled over itself as in FIG. 7J, but buffer 760K may be bent over the cuff as shown. Suture 7SK may be passed from the outer diameter OD over strut 714, the two layers of cuff 750K and the top of buffer 760K to the inner diameter ID, and then from the inner diameter back through buffer 760K and cuff 750K to the outer diameter at a position below strut 714. It will be understood that these configurations are merely exemplary and that other configurations or combinations of these arrangements are possible.

Figure 8A:
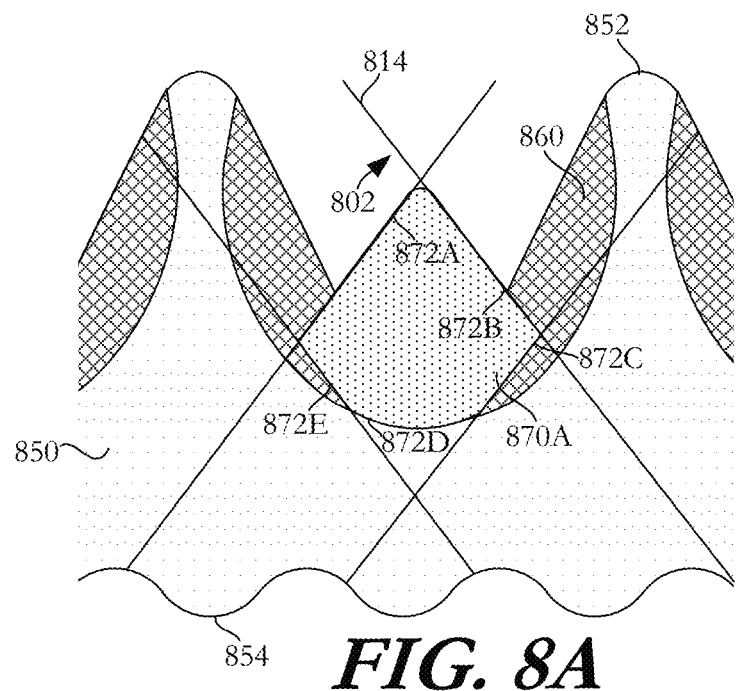
FIGS. 8A-D are schematic representations of various examples of pockets formed between a cuff and a buffer.

Through various assembly and suturing techniques, a buffer may be used to form pockets that aid in leakage prevention. FIG. 8A illustrates an assembly similar to that shown in FIG. 7G. In this embodiment, a cuff 850 extending between a first edge 852 and a second edge 854 is coupled to a buffer 860 and to a plurality of struts 814 forming a stent 802. One segment of buffer 860 may be sutured along certain struts 814 to form a pocket 870A. Specifically, pocket 870A may be formed by suturing, or otherwise coupling, the segment of buffer 860 along portions of four struts using stitch patterns 872A, 872B, 872C, 872E and to cuff 850 along contour 872D. Pocket 870A may be filled with a liquid, a gel, a powder or other media to help mitigate perivalvular leakage. One example of the filler media may be a solution of PVA sodium acrylate copolymers. Other filler media may include mechanical levers or springs, cantilevered stent component from struts or other material for helping provide a bulging of pockets 870A.

Figure 8B:
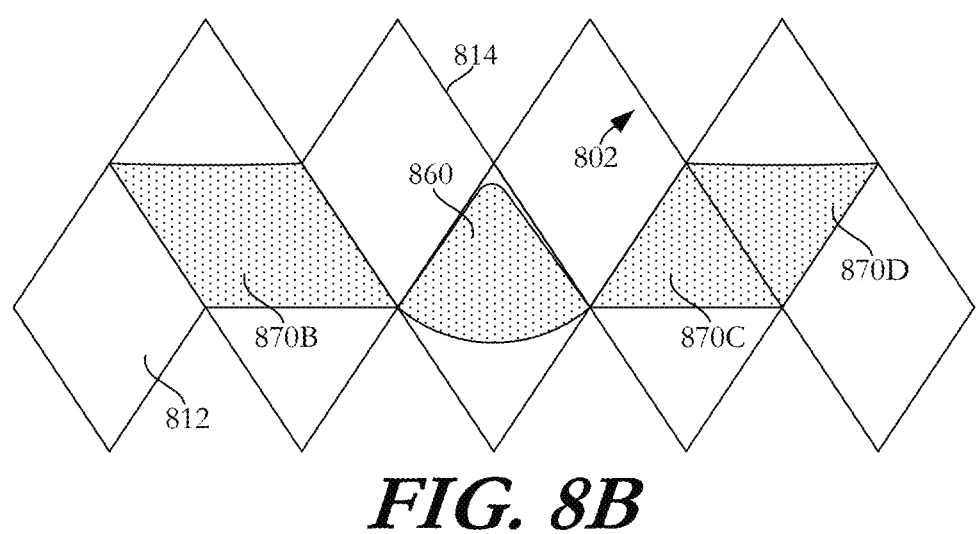
Figure 8C:
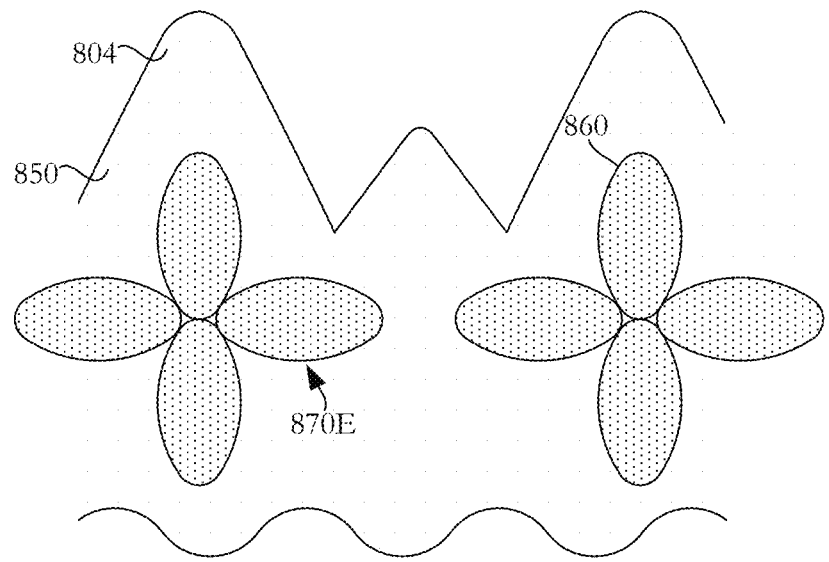
Figure 8D:
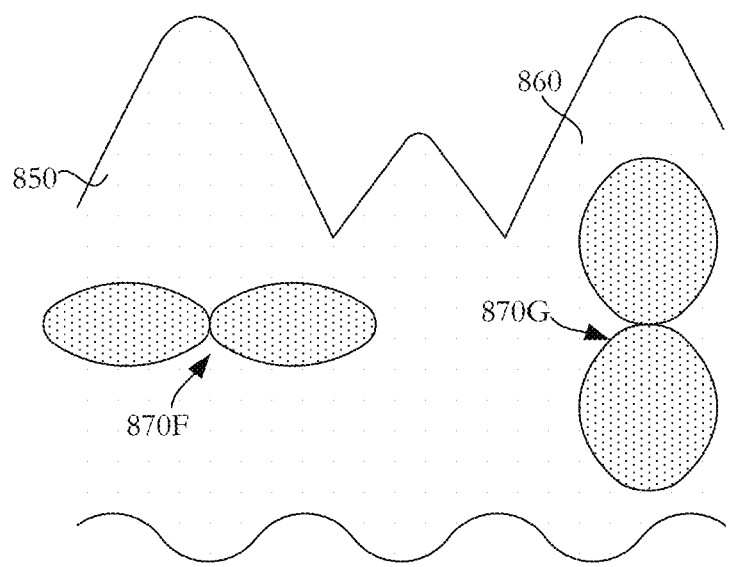

The pocket between the buffer and the cuff may be formed in a variety of shapes. For example, instead of pocket 870A shown in FIG. 8A, the pocket may be trapezoidal and span over portions of two cells 812. As shown in FIG. 8B, a trapezoidal pocket 870B may span a half of two adjacent cells 812. Alternatively, triangular pockets 870C or 870D may be formed as shown and occupy a portion (e.g., a half) of a single cell 812. Pockets 870A, 870B, 870C, 870D may follow certain struts 814 and may be formed by suturing buffer 860 to the cuff to create the desired shape. As shown in FIGS. 8C and 8D, the pockets may further take the shape of flowers 870E, which may be centered below posts 804 of cuff 850 (FIG. 8C), lemniscate 870F or figure-eights 870G (FIG. 8D). Regardless of their particular shape, the pockets, when filled, form thickened regions of the prosthetic valve cuff when implanted which help seal the valve in the native valve annulus, and thereby help to alleviate perivalvular leakage. As noted above, these pockets may include filler media that does not increase the bulk of the heart valve until implantation.

Figure 9A:
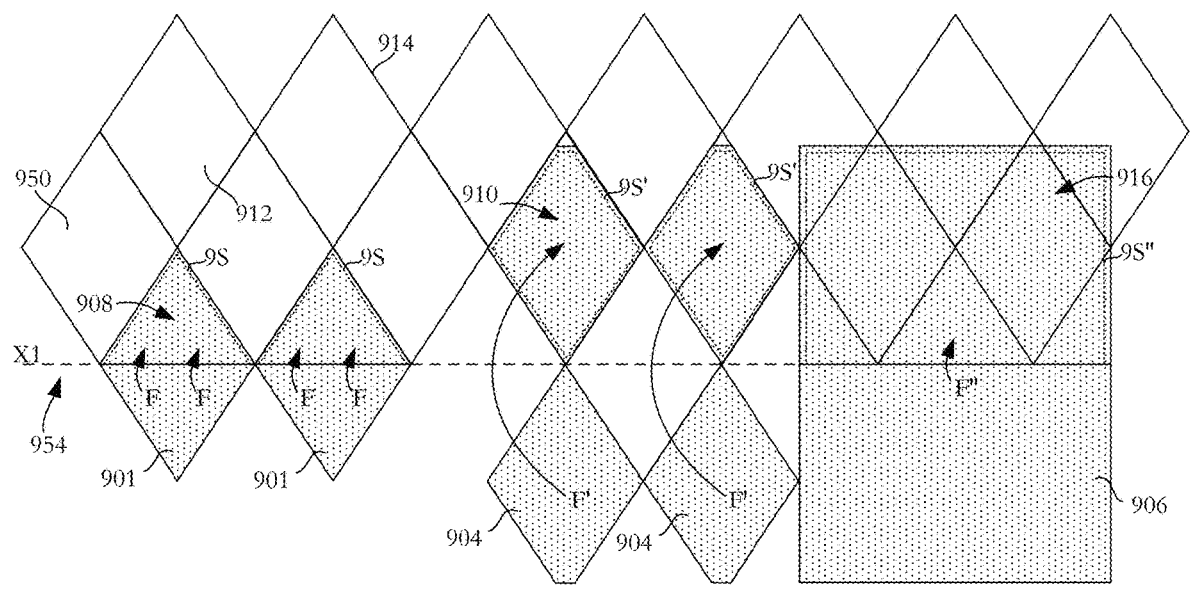
FIG. 9A is a schematic representation of a foldable extended cuff.

In addition to or instead of being formed near the outflow end of the valve assembly, the pockets may be formed near the inflow end of an aortic valve. Such pockets may be used to mitigate perivalvular leakage in susceptible areas near the inflow end 954 of the valve. FIG. 9A illustrates three different examples of forming pockets near inflow end 954. In a first example, triangular portions 901 of cuff 950 may extend beyond inflow end 954. These triangular portions 901 may be folded at lateral line X1 in the direction of arrows F to overlie the remainder of cuff 950, and may be sewn to the cuff and/or stent struts 914 with suture pattern 9S to form triangular pockets 908. In a second example, substantially diamond-shaped portions 904 of cuff 950 may extend beyond inflow end 954. These partial diamond-shaped portions 904 may be folded at lateral line X1 in the direction of arrows F' to overlie the remainder of cuff 950 within a cell 912, and may be sewn to the cuff and/or stent struts 914 with suture pattern 9S' to form substantially diamond-shaped pockets 910. It will be understood that in some variations, full diamonds, half diamonds or any portion of a diamond may be used to form pockets with the cuff. In a third example, a rectangular portion 906 of cuff 950 may extend beyond inflow end 954. Rectangular portion 906 may be folded at lateral line X1 in the direction of arrow F" to overlie the remainder of cuff 950 in an area occupying a number of partial cells 912, and may be sewn to the cuff and/or stent struts 914 with suture pattern 9S" to form rectangular pockets 916.

Triangular pockets 908, substantially diamond-shaped pockets 910 and rectangular pockets 916 may be filled with any suitable filler material as discussed above with reference to FIG. 8A. Moreover, by using pockets 908, 910 and/or 916 instead of an additional cuff layer, the crimp profile of the resulting prosthetic heart valve may be reduced. It will be understood that any combination of the pocket shapes described above, or any other pocket shapes, may be used to help mitigate perivalvular leakage, and that the pockets may alternate between shapes, for example, between triangular and rectangular pocket shapes, around the periphery of cuff 950. It will also be understood that instead of extending cuff 950 beyond the inflow end 954 of the valve, a discrete buffer material may be sewn to the cuff near inflow end 954 to create the pockets described above.

Pockets may be created in various shapes at the inflow end 954 of the aortic valve as described above, and may be attached to cuff 950 and/or stent struts 914 in a variety of configurations, illustrated in FIGS. 9B-G. In a first example, cuff 950 may be disposed on the outer diameter OD of stent 902, and edge 950B of cuff 950 may be folded under the end of the stent to the inner diameter ID (FIG. 9B). In a second example, cuff 950 may be disposed on the inner diameter ID of stent 902, and edge 950C of cuff 950 may be folded under the end of the stent to the outer diameter OD (FIG. 9C). In a third example, cuff 950 may be disposed on the outer diameter OD of stent 902 and edge 950D of cuff 950 may be folded over the rest of the cuff on the outer diameter OD (FIG. 9D). In a fourth example, cuff 950 may be disposed on the inner diameter ID of stent 902, and edge 950E of cuff 950 may be folded over the rest of the cuff on the inner diameter ID (FIG. 9E). In each of the foregoing examples, the folded edge of the cuff may be secured to the remaining portion of the cuff and/or to the struts of stent 902 by suturing or in other ways known in the art.

In two other configurations shown in FIGS. 9F and 9G, the cuff is folded to both inner diameter ID and outer diameter OD. FIG. 9F illustrates cuff 950 disposed on the outer diameter OD of stent 902. Portions 950F' of cuff 950 may be folded under the end of stent 902 to the inner diameter ID, while other portions 950F of the cuff may be folded over the remainder of the cuff on the outer diameter OD. FIG. 9F illustrates the opposite configuration in which cuff 950 is disposed on the inner diameter ID of stent 902. Portions 950G of cuff 950 may be folded under the end of stent 902 to the outer diameter OD, while other portions 950G' of the cuff may be folded over the remainder of the cuff on the inner diameter ID.

FIG. 9H illustrates a cuff 950H having portions folded to both the inner and outer diameters. Triangular portions 901 of cuff 950H may be folded in the direction of arrows F1 toward the outer diameter of stent 902, while substantially diamond-shaped portions 904 of the cuff may be folded in the direction of arrows F2 toward the inner diameter of the stent.

Figure 10:
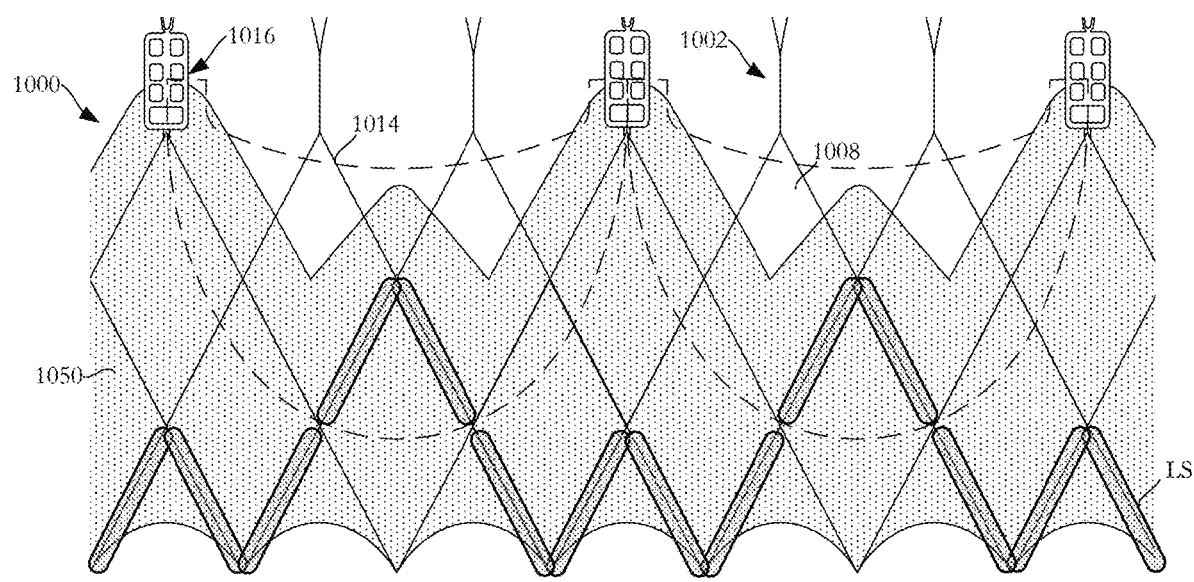
FIG. 10 is a schematic representation of one possible suture pattern for attaching a buffer to a cuff.

Another technique to reduce the crimp profile of a prosthetic heart valve is to reduce the number of suture wraps that attach the cuff to struts of the stent. Reference will be made to FIG. 10 to illustrate this reduction in suture usage. As shown, prosthetic heart valve 1000 includes a cuff 1050 coupled to struts 1014 of stent 1002. Leaflets 1008 are attached to stent 1002 at least via commissure features 1016.

Under normal operation of heart valve 1000, certain struts experience lower stress than others. Specifically, areas of low stress are outlined by regions LS. To reduce the overall crimp profile of the valve, fewer sutures may be used in these areas than in others. For example, cuff 1050 may be attached to each strut 1014 by six suture wraps in all areas except the designated low-stress areas, in which four suture wraps may be used. Thus, any number of suture wraps may be used to attach the cuff to any strut and fewer suture wraps may be used in the designated low-stress regions LS.

Figure 11:
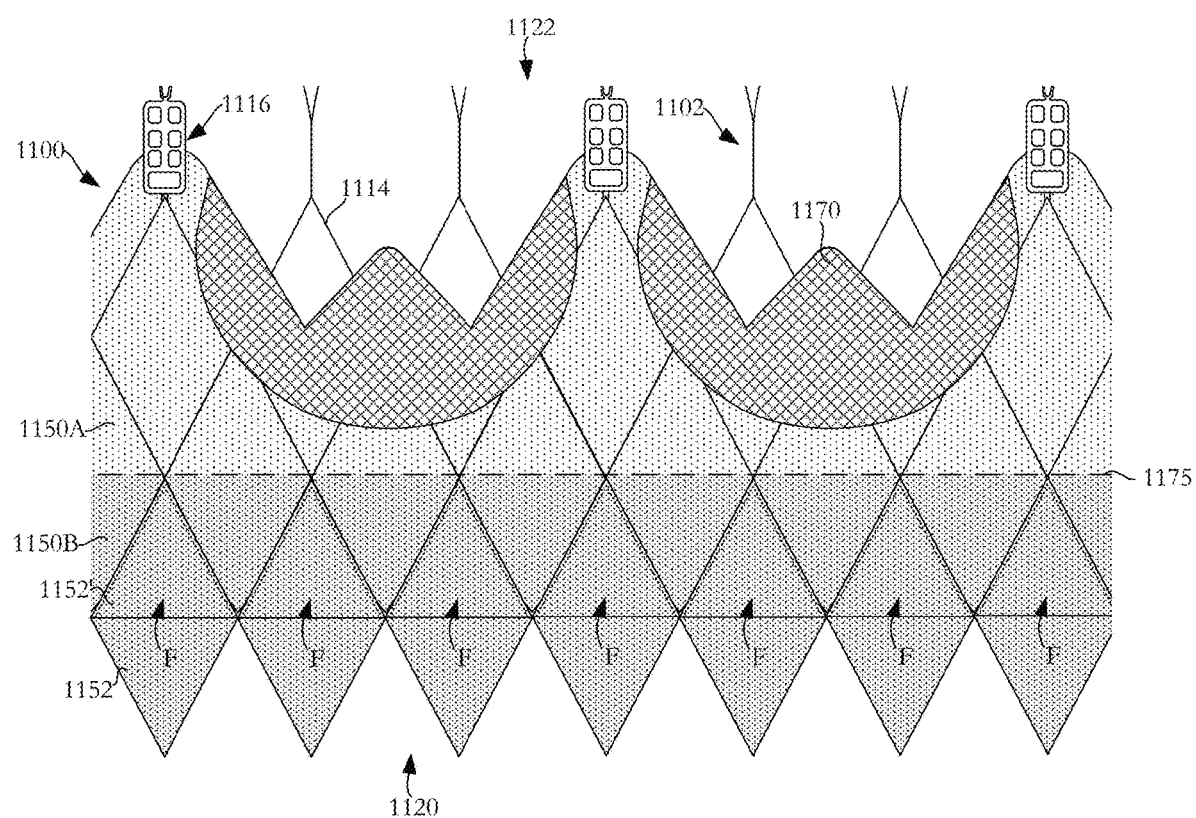
FIG. 11 is a schematic representation of a heart valve including an upper and lower buffer layer.

Another mechanism for mitigating perivalvular leakage is to provide the prosthetic heart valve with multiple cuffs. As shown in FIG. 11, heart valve 1100 may include a pair of cuffs 1150A, 1150B attached to struts 1114 of stent 1102. First cuff 1150A may be attached to stent 1102 near commissure features 1116 and the outflow edge 1122 of the valve assembly, and may form pockets 1170 similar to those described with reference to FIGS. 7A-8A. Second cuff 1150B may be attached to stent 1102 near the inflow end 1102 of the valve assembly, and may extend beyond the inflow end by triangular portions 1152, which fold up in the direction of arrows F on either the inner diameter or outer diameter of the valve assembly. First cuff 1150A and second cuff 1150B may be attached to one another by suturing or other suitable means at seam 1175. These cuffs may be formed from any of the cuff materials described above (e.g., natural materials or synthetic materials). First and second cuffs 1150A, 1150B may be formed from the same material or from different materials. For example, first cuff 1150A may be formed from porcine tissue while second cuff 1150B may be formed from a synthetic fabric, or vice versa.

Figure 12:
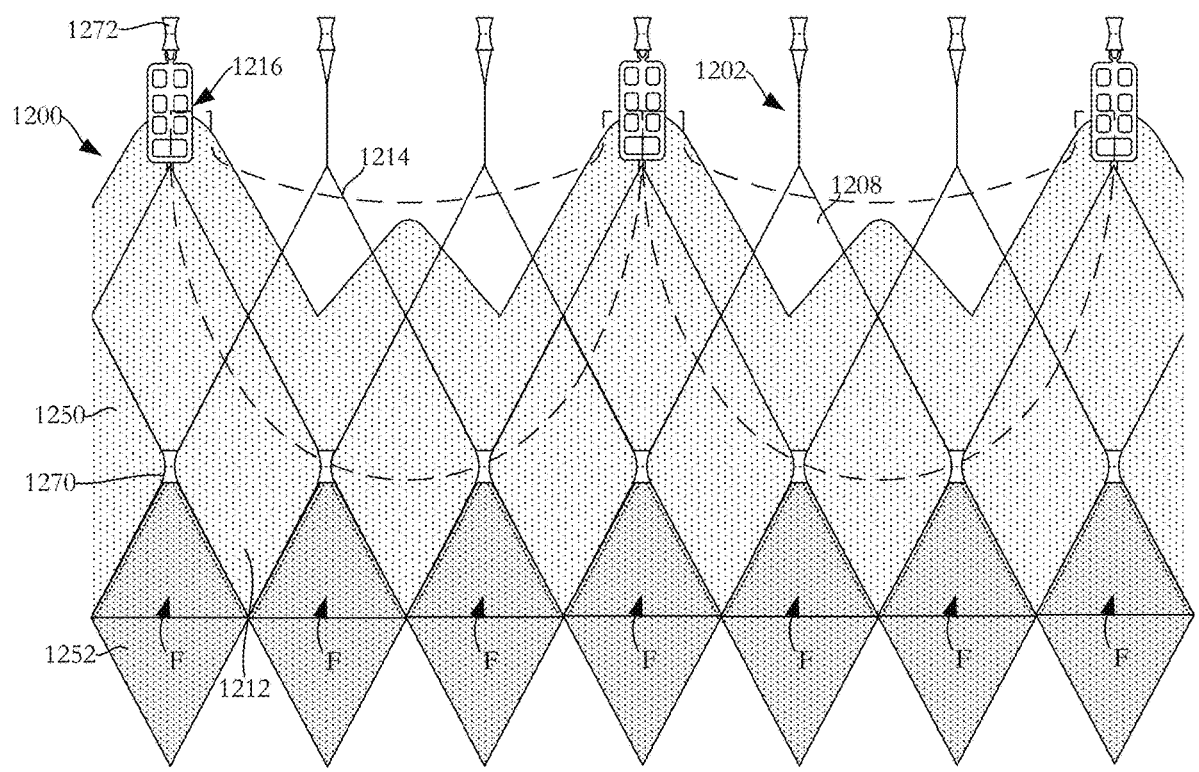
FIG. 12 is a schematic representation of a heart valve including an extended cuff and hinges.

To offset any possible increase in crimp profile, certain features may be added to the prosthetic heart valve to facilitate delivery. FIG. 12 illustrates prosthetic heart valve 1200 having cuff 1250 and leaflets 1208 attached to stent 1202 at select struts 1214 and commissure features 1216. Cuff 1250 may include additional triangular portions 1252 that may be folded up in the direction of arrows F as described above. To aid in delivery, stent 1202 may include hinges 1270 at the midsection of the lowermost row of cells 1212 so that the stent may slightly bend at this position during delivery. Similar hinges 1272 may be added at a level above commissures 1216 to provide additional flexibility to the stent 1202.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve comprising:
    a collapsible and expandable stent having a plurality of cells formed by struts and extending between an inflow end to an outflow end;
    a cuff disposed on a luminal surface of the stent and extending between a proximal end and a distal end, the proximal end of the cuff being nearer the inflow end of the stent than is the distal end of the cuff; and
    a plurality of leaflets coupled to the cuff,
    wherein a portion of the distal end of the cuff is folded over a first one of the struts of the stent to form an inner cuff layer and an outer cuff layer at the folded portions of the cuff, and
    wherein a first suture wrap passes through one of the plurality of leaflets, the inner cuff layer at a first location, the outer cuff layer, and again through the inner cuff layer at a second location.

2. The prosthetic heart valve of claim 1, wherein the cuff includes a mid-portion between the proximal and distal ends of the cuff, the mid-portion of the cuff being positioned only on the luminal surface of the stent.

3. The prosthetic heart valve of claim 1, wherein the outer cuff layer at the folded portion of the cuff includes a distal edge facing the inflow end of the stent.

4. The prosthetic heart valve of claim 1, wherein the cuff is coupled to the stent via a single suture.

5. The prosthetic heart valve of claim 1, wherein the cuff is coupled to the stent via a plurality of sutures.

6. The prosthetic heart valve of claim 1, wherein a second suture wrap wraps around the folded portion of the cuff and passes through the outer cuff layer and the inner cuff layer so that the first suture wrap also wraps around the first one of the struts.

7. The prosthetic heart valve of claim 1, wherein the first suture wrap passes through two layers of the one of the plurality of leaflets.

8. The prosthetic heart valve of claim 1, wherein a third suture wrap passes through the cuff at a first location and a second location so that the third suture wrap wraps around a second one of the struts, the second one of the struts being positioned nearer the inflow end of the stent than is the first one of the struts.

9. The prosthetic heart valve of claim 1, wherein the first suture wrap directly secures one of the plurality of leaflets to the inner and outer cuff layers.

10. The prosthetic heart valve of claim 9, wherein the first suture wrap passes through two layers of the one of the plurality of leaflets.

11. The prosthetic heart valve of claim 9, wherein a second suture wrap directly secures the inner and outer cuff layers to the one of the struts.

12. The prosthetic heart valve of claim 9, wherein a second suture wrap directly secures the inner cuff layer to the outer cuff layer.

13. The prosthetic heart valve of claim 9, wherein a second suture wrap directly secures the cuff to a second one of the struts, the second one of the struts being positioned nearer the inflow end of the stent than is the first one of the struts.

14. The prosthetic heart valve of claim 13, wherein the second suture wrap passes only through one layer of the cuff.

15. The prosthetic heart valve of claim 1, wherein all portions of the cuff other than the folded portions are a single layer.

* * * * *